(12) United States Patent
Duinat et al.

(10) Patent No.: US 10,814,059 B2
(45) Date of Patent: Oct. 27, 2020

(54) SYRINGE PACKAGING SYSTEM

(71) Applicant: Fresenius Kabi Deutschland GmbH, Bad Homburg (DE)

(72) Inventors: Brigitte Duinat, Grenoble (FR); Charles D. Shermer, Raleigh, NC (US); Luc Dorelon, St. Martin de la Cluze (FR); Tracy Hottovy, Wilson, NC (US); James Kenneth Proctor, Nashville, NC (US); Robert Speek, Highland Park, IL (US); Jonathan Wacks, Skokie, IL (US)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 15/868,816

(22) Filed: Jan. 11, 2018

(65) Prior Publication Data

US 2018/0126065 A1 May 10, 2018

Related U.S. Application Data

(63) Continuation-in-part of application No. 15/206,029, filed on Jul. 8, 2016, now Pat. No. 10,064,998.
(Continued)

(51) Int. Cl.
*A61M 5/00* (2006.01)
*A61M 5/31* (2006.01)
(Continued)

(52) U.S. Cl.
CPC .......... *A61M 5/002* (2013.01); *A61M 5/3137* (2013.01); *A61M 5/31505* (2013.01);
(Continued)

(58) Field of Classification Search
CPC .......... A61M 5/00; A61M 5/002; A61M 5/28; A61M 5/31; A61M 5/3137; A61M 5/315;
(Continued)

(56) References Cited

U.S. PATENT DOCUMENTS 3,342,319 A 9/1967 Faulseit
4,671,408 A 6/1987 Raines et al.
(Continued)

FOREIGN PATENT DOCUMENTS

WO WO 2001/023017 A2 4/2001
WO WO 2006/018626 A1 2/2006

OTHER PUBLICATIONS

European Patent Office, International Search Report in International Application No. PCT/IB2016/054126 (dated Sep. 26, 2016).
(Continued)

*Primary Examiner* — Bryon P Gehman
(74) *Attorney, Agent, or Firm* — Leydig, Voit & Mayer, Ltd.

(57) ABSTRACT

A syringe packaging system that includes a tube and a cap for enclosing a pre-filled syringe, wherein the tube includes a cut flange and the cap includes a cut skirt. When the pre-filled syringe is enclosed within the tube and cap, the tube and cap are maintained together by a plurality of crush ribs on the cap or by a film secured to a portion of the tube and a portion of the cap. An injection molding gate is located on the sidewall of the tube to prevent diversion or tampering with the pre-filled syringe.

18 Claims, 36 Drawing Sheets

Related U.S. Application Data

(60) Provisional application No. 62/191,052, filed on Jul. 10, 2015.

(51) Int. Cl.
*A61M 5/315* (2006.01)
*A61M 5/32* (2006.01)
*A61M 5/50* (2006.01)

(52) U.S. Cl.
CPC ........ *A61M 5/3202* (2013.01); *A61M 5/5086* (2013.01); *A61M 2005/3104* (2013.01); *A61M 2005/3142* (2013.01)

(58) Field of Classification Search
CPC .. A61M 5/31505; A61M 5/32; A61M 5/3202; A61M 2005/3104; A61M 2005/3142; A61M 5/50; A61M 5/5086; B65D 75/00; B65D 81/20; B65D 81/26; B65D 81/266; B65D 81/267; B65D 81/268; B65D 83/00; B65D 85/00; B65D 85/08; B65D 85/30
USPC ................................. 206/364, 365
See application file for complete search history.

(56) References Cited

U.S. PATENT DOCUMENTS

| | | | |
|---|---|---|---|
| 4,877,132 A * | 10/1989 | Makris | A61M 5/002 206/364 |
| 4,979,616 A | 12/1990 | Clanton | |
| 5,417,326 A * | 5/1995 | Winer | A61M 5/002 206/365 |
| 5,519,931 A | 5/1996 | Reich | |
| 5,566,828 A | 10/1996 | Claes et al. | |
| 5,615,772 A | 4/1997 | Naganuma | |
| 6,073,759 A | 6/2000 | Lalmborne et al. | |
| 6,368,305 B1 | 4/2002 | Dutton | |
| 6,595,362 B2 | 7/2003 | Penney et al. | |
| 6,808,507 B2 | 10/2004 | Roser | |
| 6,929,126 B1 | 8/2005 | Herbert | |
| 7,597,196 B2 | 10/2009 | Langone | |
| 7,875,007 B2 * | 1/2011 | Perot | A61F 9/0017 604/235 |
| 8,043,267 B2 * | 10/2011 | Nanba | A61M 5/28 604/190 |
| 9,144,465 B2 | 9/2015 | Hunkeler et al. | |
| 9,333,146 B2 | 5/2016 | Perot et al. | |
| 9,333,288 B2 | 5/2016 | Hilliard et al. | |
| 9,333,289 B1 | 5/2016 | Hirschmann et al. | |
| 9,586,011 B2 * | 3/2017 | Roberts | A61M 5/3271 |
| 10,052,437 B2 | 8/2018 | Duinat et al. | |
| 10,064,998 B2 | 9/2018 | Duinat et al. | |
| 10,159,796 B2 | 12/2018 | Schiff et al. | |
| 10,220,150 B2 * | 3/2019 | Ito | A61M 5/31 |
| 10,525,209 B2 * | 1/2020 | Matsui | B29C 45/36 |
| 2004/0069667 A1 | 4/2004 | Tomellini et al. | |
| 2011/0087173 A1 | 4/2011 | Sibbitt, Jr. et al. | |
| 2013/0081974 A1 | 4/2013 | Hilliard et al. | |
| 2013/0082057 A1 | 4/2013 | Schiff et al. | |
| 2014/0078854 A1 | 3/2014 | Head et al. | |
| 2017/0007770 A1 | 1/2017 | Duinat et al. | |
| 2017/0007771 A1 | 1/2017 | Duinat et al. | |
| 2018/0344935 A1 | 12/2018 | Duinat et al. | |
| 2018/0344938 A1 | 12/2018 | Duinat et al. | |

OTHER PUBLICATIONS

European Patent Office, Written Opinion in International Application No. PCT/IB2016/054126 (dated Sep. 26, 2016).
U.S. Appl. No. 16/103,661, filed Aug. 14, 2018.
U.S. Appl. No. 16/057,279, filed Aug. 7, 2018.

* cited by examiner

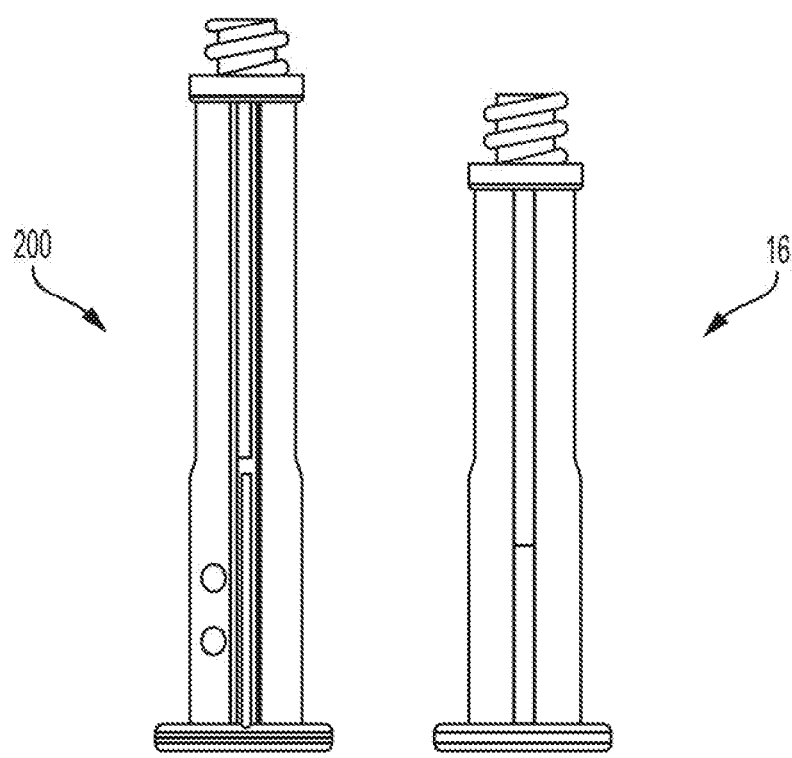

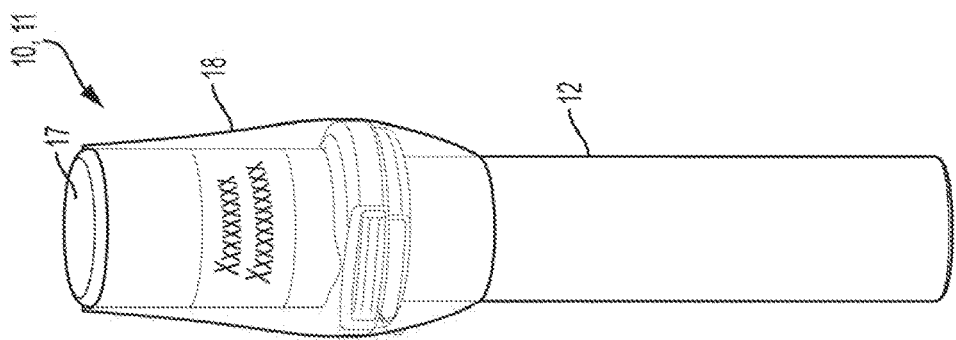
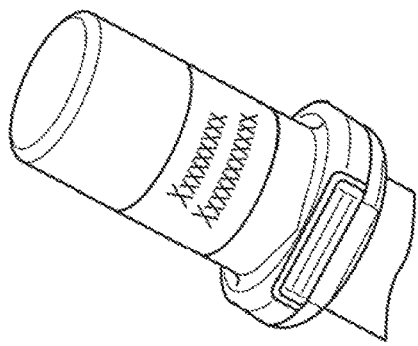
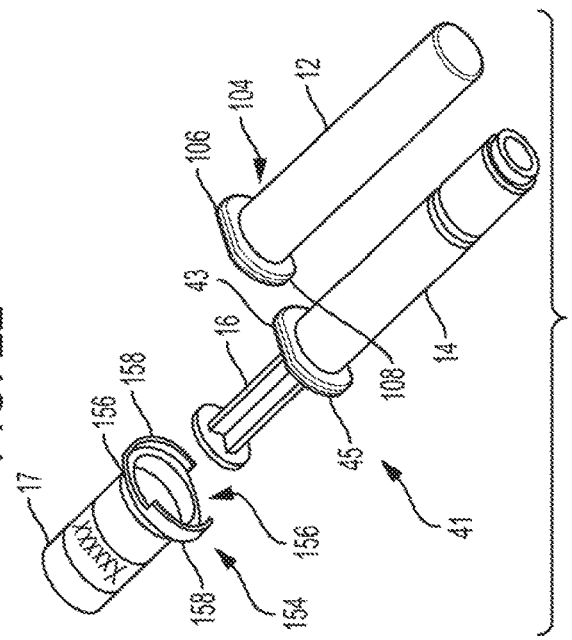
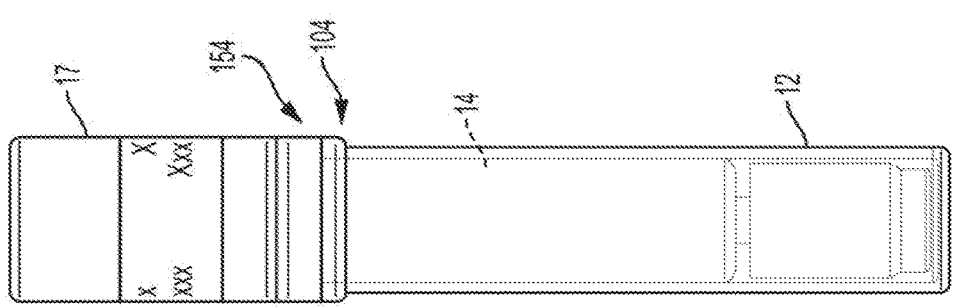
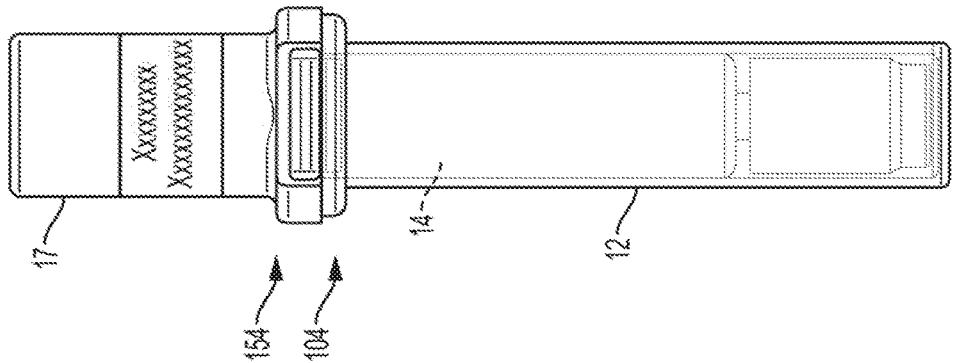
FIG. 24
FIG. 22
FIG. 23
FIG. 21
FIG. 20

SYRINGE PACKAGING SYSTEM

CROSS-REFERENCE TO RELATED APPLICATIONS

This patent application is a continuation-in-part of co-pending U.S. patent application Ser. No. 15/206,029 filed Jul. 8, 2016, which claims the benefit of U.S. Provisional Application No. 62/191,052, filed Jul. 10, 2015, all of which are incorporated herein by reference in their entirety.

BACKGROUND OF THE INVENTION

Field of the Disclosure

The present disclosure relates generally to a syringe assembly adapted for delivery of a fluid. More particularly, the present disclosure relates to a syringe packaging system that allows for reduced storage space of a syringe assembly.

Description of the Related Art

Syringe assemblies, and in particular hypodermic syringes, are well known in the medical field for dispensing fluids, such as medications. A conventional syringe typically includes a syringe barrel with an opening at one end and a plunger mechanism disposed through the opposite end. The plunger mechanism typically includes a plunger rod extending through the barrel, with a plunger head or stopper disposed at the end of the plunger rod within the syringe barrel, and with a finger flange at the other end of the plunger rod extending out of the syringe barrel. In use, the plunger rod is retracted through the syringe barrel to aspirate or fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the syringe barrel for attachment with a fluid line of a patient. Upon application of a force to depress the plunger rod and stopper through the syringe barrel towards the front end of the syringe barrel, the contents of the syringe are thereby forced out of the syringe barrel through the opening at the front end for delivery to the patient.

Commonly, hypodermic syringes may be packaged as "pre-filled" devices, wherein the syringe is pre-filled with medication prior to being packaged and delivered to the patient. In this manner, the need for the user to fill the device prior to injection is eliminated, thereby saving time and maintaining consistent volumes for delivery.

However, packaging of such pre-filled syringes tends to be bulky and difficult to ship and store. Pre-filled syringes and pre-filled metered dose syringes are often filled with fluids, such as a medication, at a production facility, packaged, and then shipped to a medical facility. Once at the facility, these syringes are often placed in controlled storage and/or locked cabinets to reduce theft of the syringes themselves and/or of the contents of these syringes. The space within these controlled storage locations is often limited, thus there is a need for a syringe assembly that has a smaller packaging footprint to reduce the amount of storage space required for containing the syringe.

SUMMARY OF THE INVENTION

In accordance with an embodiment of the present invention, a syringe packaging system includes a tube and a cap for enclosing a pre-filled syringe. The tube includes a tube cut flange and the cap includes a cut skirt. With a syringe barrel contained within the tube, a syringe barrel cut flange is aligned with the tube cut flange. With the pre-filled syringe enclosed within the tube and the cap, the cut skirt of the cap surrounds the syringe barrel cut flange. In one embodiment, a film is securable to a portion of the tube and a portion of the cap to connect the tube and the cap with the pre-filled syringe enclosed within the cap and the tube.

In accordance with an embodiment of the present invention, a syringe packaging system includes a pre-filled syringe including a syringe barrel having a proximal end, a distal end, and a sidewall extending therebetween and defining a chamber, the proximal end having a syringe barrel cut flange; and a packaging member enclosing the pre-filled syringe, the packaging member including a tube having a proximal end and a distal end, the proximal end including a tube cut flange, with the syringe barrel contained within the tube, the syringe barrel cut flange is aligned with the tube cut flange.

In one configuration, the syringe barrel cut flange includes a first flat wall portion and a first arcuate wall portion. In another configuration, the tube cut flange includes a second flat wall portion and a second arcuate wall portion. In yet another configuration, the syringe packaging system includes a cap having a first end and a second end, the second end including a cut skirt. In one configuration, the cut skirt includes a third flat wall portion and a third arcuate wall portion. In another configuration, with the pre-filled syringe enclosed within the packaging member, the cut skirt of the cap surrounds the syringe barrel cut flange. In yet another configuration, the syringe packaging system includes a film securable to a portion of the tube and a portion of the cap to connect the tube and the cap with the pre-filled syringe enclosed within the cap and the tube. In one configuration, the distal end of the tube is closed.

In accordance with another embodiment of the present invention, a syringe packaging system includes a pre-filled syringe, comprising: a syringe barrel having a proximal end, a distal end, and a sidewall extending therebetween and defining a chamber, the proximal end having a syringe barrel cut flange; a fluid disposed within the chamber of the syringe barrel; a stopper slidably disposed within the chamber of the syringe barrel; and a plunger rod having a proximal end and a distal end engageable with a portion of the stopper; and a packaging member enclosing the pre-filled syringe, the packaging member comprising: a tube having a proximal end and a distal end, the proximal end including a tube cut flange; a cap having a first end and a second end, the second end including a cut skirt; and a film securable to a portion of the tube and a portion of the cap to connect the tube and the cap with the pre-filled syringe enclosed within the cap and the tube.

In one configuration, the syringe barrel cut flange includes a first flat wall portion and a first arcuate wall portion. In another configuration, the tube cut flange includes a second flat wall portion and a second arcuate wall portion. In yet another configuration, the cut skirt includes a third flat wall portion and a third arcuate wall portion. In one configuration, with the pre-filled syringe enclosed within the packaging member, the cut skirt of the cap surrounds the syringe barrel cut flange. In another configuration, with the syringe barrel contained within the tube, the syringe barrel cut flange is aligned with the tube cut flange. In yet another configuration, the distal end of the tube is closed.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 11 is a front view of a standard plunger rod.

FIG. 12 is a front view of a plunger rod in accordance with an embodiment of the present invention.

FIG. 20 is an elevation view of a syringe packaging system in accordance with an embodiment of the present invention.

FIG. 21 is an elevation view of a syringe packaging system in accordance with an embodiment of the present invention.

FIG. 22 is a perspective view of a proximal end of a syringe packaging system in accordance with an embodiment of the present invention.

FIG. 23 is an exploded, perspective view of a syringe packaging system in accordance with an embodiment of the present invention.

FIG. 24 is an assembled, perspective view of a syringe packaging system in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
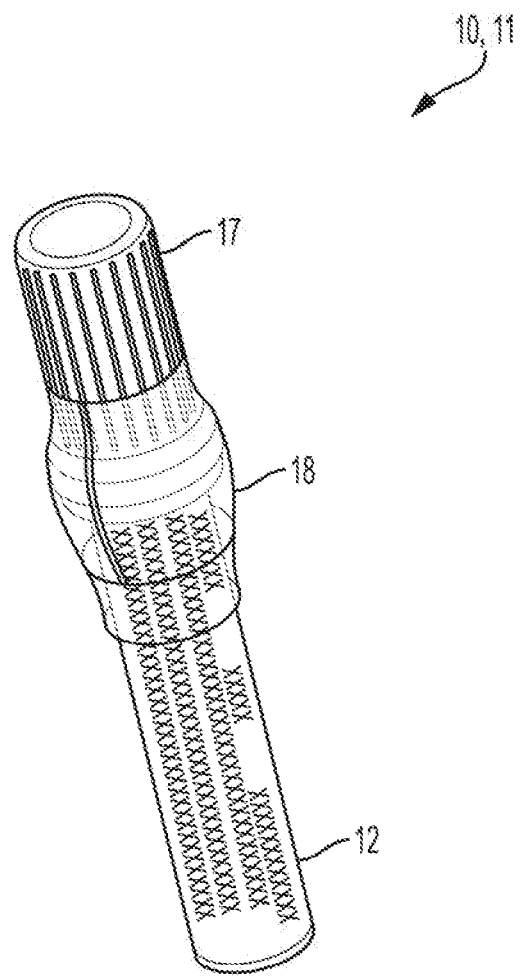
FIG. 1 is a perspective view of a syringe packaging system in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

In the following discussion, "distal" refers to a direction generally toward an end of a syringe or a syringe assembly adapted for contact with a patient and/or engagement with a separate device such as a needle assembly or IV connection assembly, and "proximal" refers to the opposite direction of distal, i.e., away from the end of a syringe or a syringe assembly adapted for engagement with the separate device. For purposes of this disclosure, the above-mentioned references are used in the description of the components of a syringe or a syringe assembly in accordance with the present disclosure.

FIGS. 1-39 illustrate exemplary embodiments of the present disclosure. Referring to FIGS. 1-39, a syringe packaging system 10 includes a packaging member or packaging assembly 11 having a tube 12, a cap 17, and a film 18; and a syringe or a syringe assembly 13 including a syringe barrel 14, a plunger rod 16, and a stopper 19. The tube 12 and cap 17 of the syringe packaging system 10 provides a packaging member for a pre-filled syringe, such as syringe 13. The tube 12 and cap 17 of the present disclosure allows for reduced storage space of a pre-filled syringe. For example, the tube 12 and cap 17 allows for reduced storage space of a pre-filled syringe in an automated dispensing cabinet.

Figure 15:
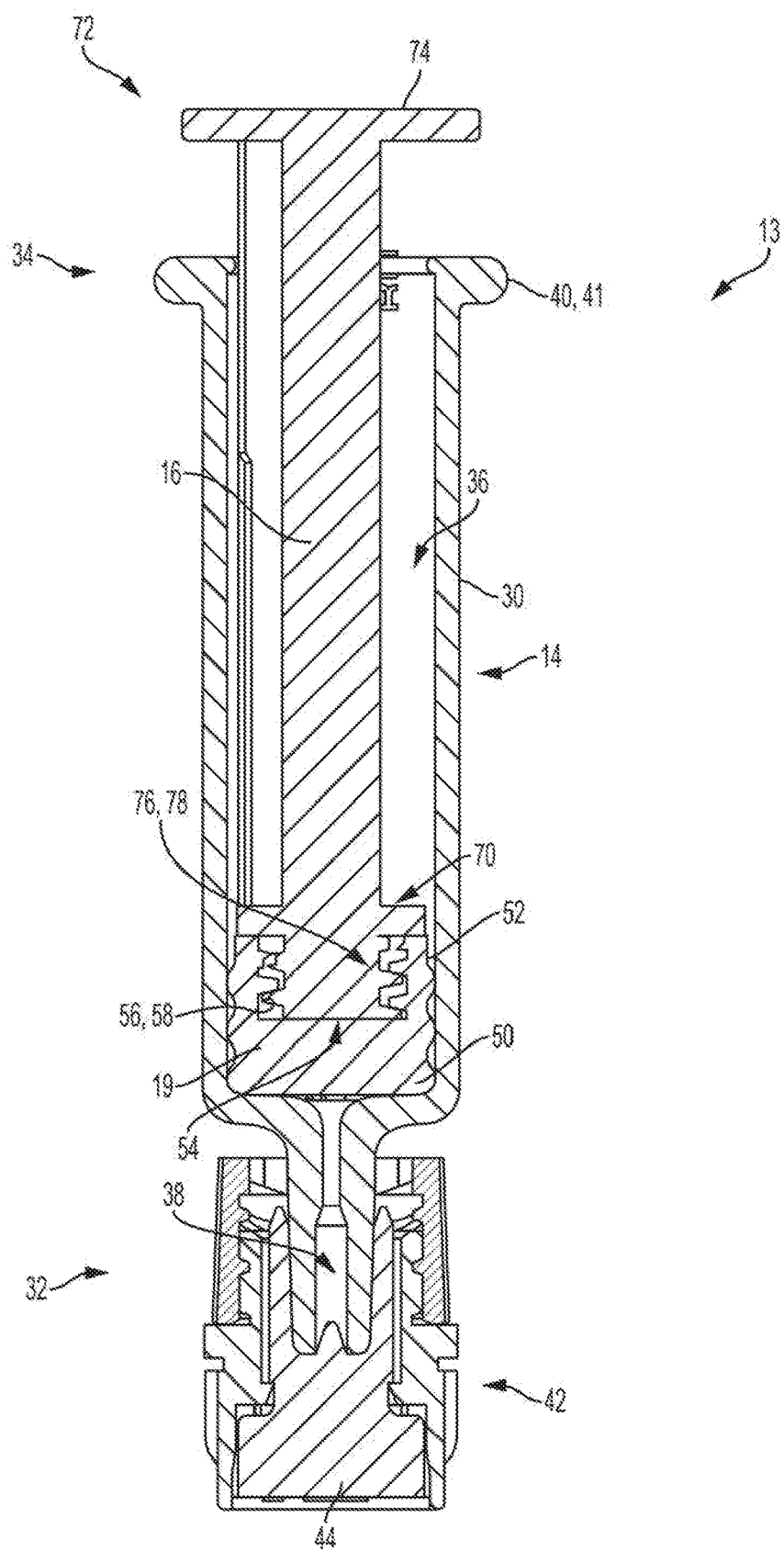
FIG. 15 is a cross-sectional view of a syringe in a first position in accordance with an embodiment of the present invention.
Figure 16:
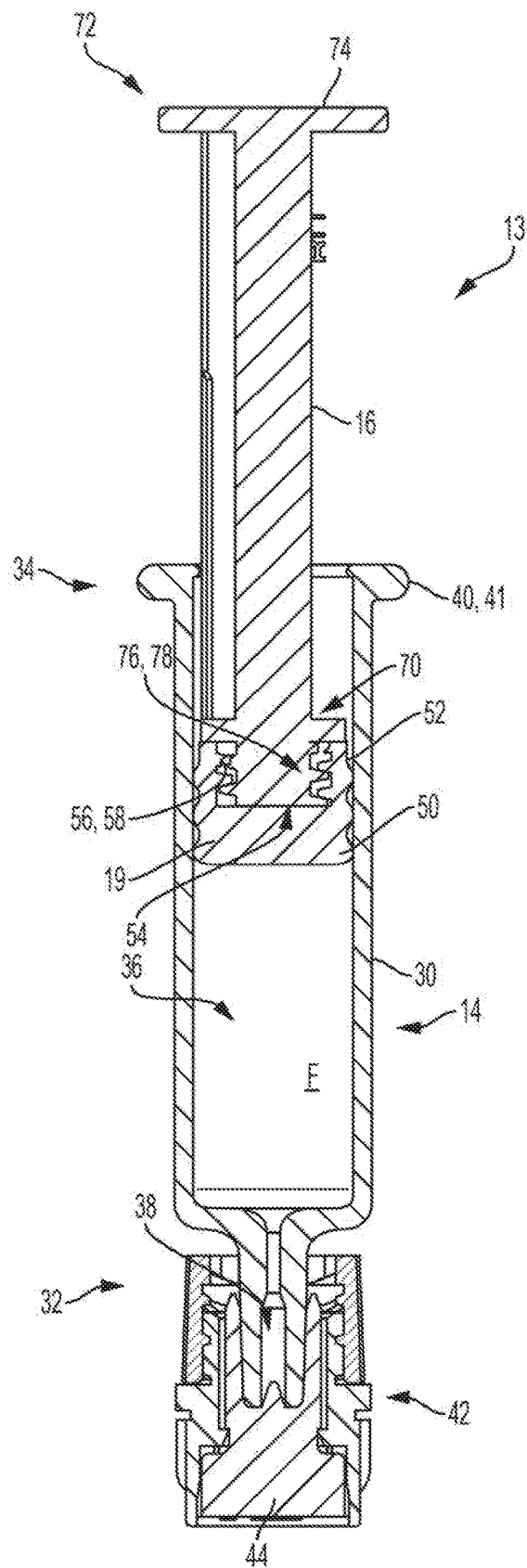
FIG. 16 is a cross-sectional view of a syringe in a second position in accordance with an embodiment of the present invention.

Referring to FIGS. 15 and 16, in one embodiment, syringe assembly 13 includes syringe barrel 14, plunger rod 16, and a stopper 19. Syringe assembly 13 may be adapted for dispensing and delivery of a fluid and/or collection of a fluid. For example, syringe assembly 13 may be used for injection or infusion of fluid such as a medication or drug into a patient. Syringe assembly 13 is contemplated for use in connection with a needle, such as by connecting syringe assembly 13 to a separate needle assembly (not shown), or alternatively for connection with an intravenous (IV) connection assembly (not shown). It can be appreciated that the present disclosure can be used with any type of syringe assembly, particularly those which are placed in a controlled storage environment in which storage space is limited. These types of syringes include traditional pre-filled syringe assemblies, metered dose syringes, aspiration syringes for withdrawing fluid from a patient or medication from a container, and the like.

In one embodiment, the tube 12 and cap 17 can be designed for a syringe 13 that is a cut flange syringe. In other embodiments, the tube 12 and cap 17 can be designed for a syringe 13 that is a round flange syringe. In other embodiments, the tube 12 and cap 17 can be designed for other syringes.

Figure 17:
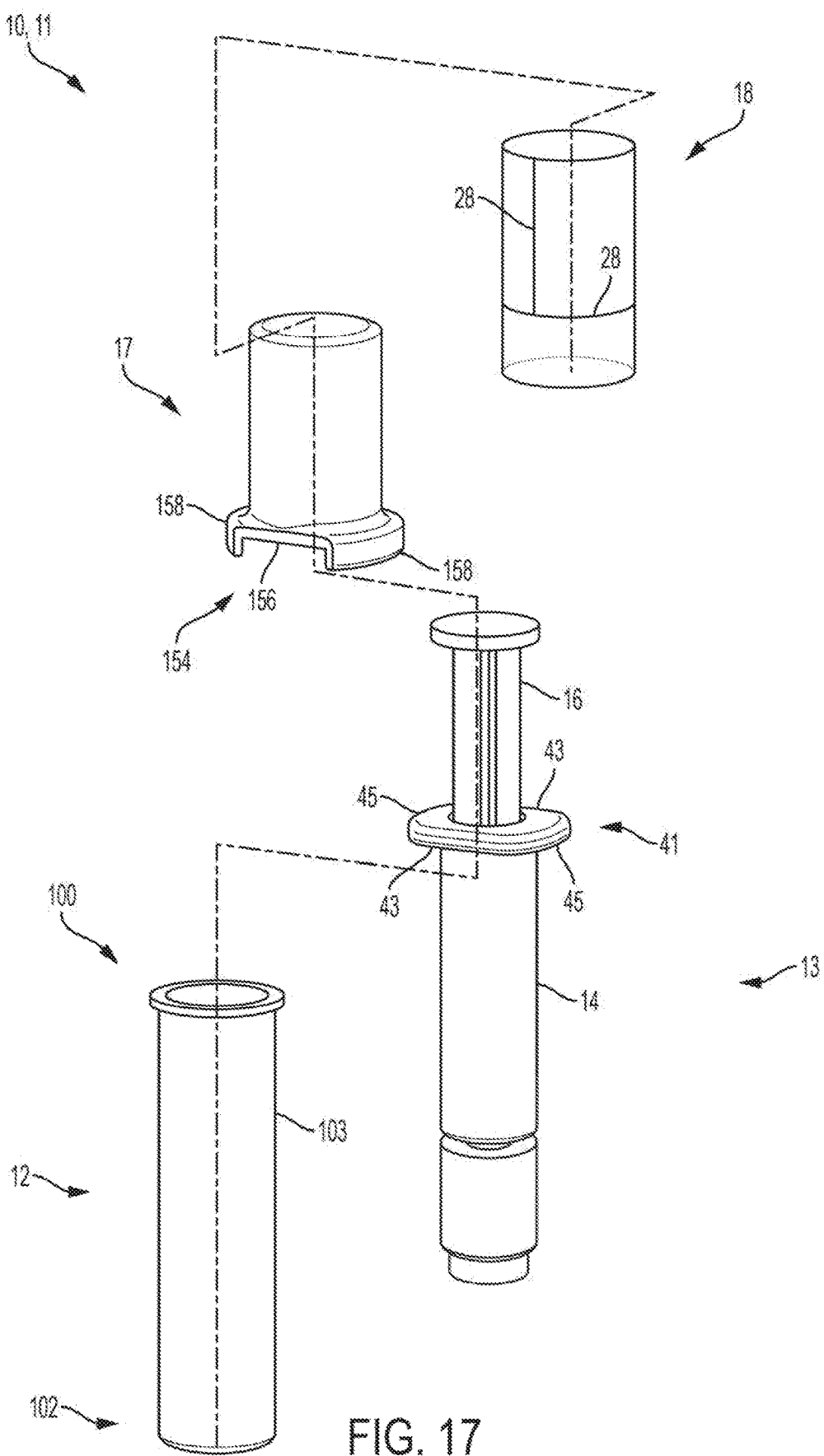
FIG. 17 is an exploded, perspective view of a syringe packaging system in accordance with an embodiment of the present invention.
Figure 18:
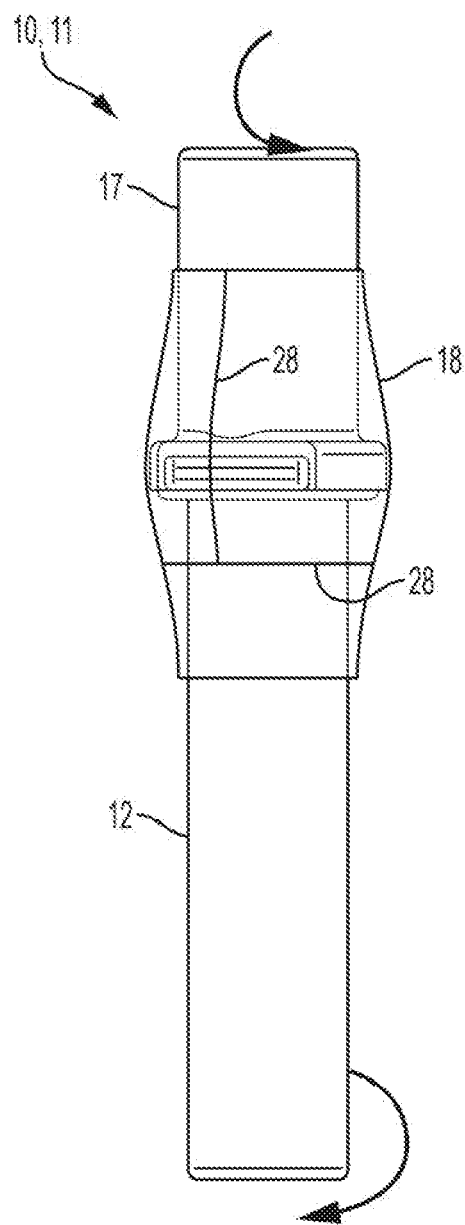
FIG. 18 is an assembled, front view of the syringe packaging system of FIG. 17, with a film connecting a tube and a cap in accordance with an embodiment of the present invention.
Figure 19:
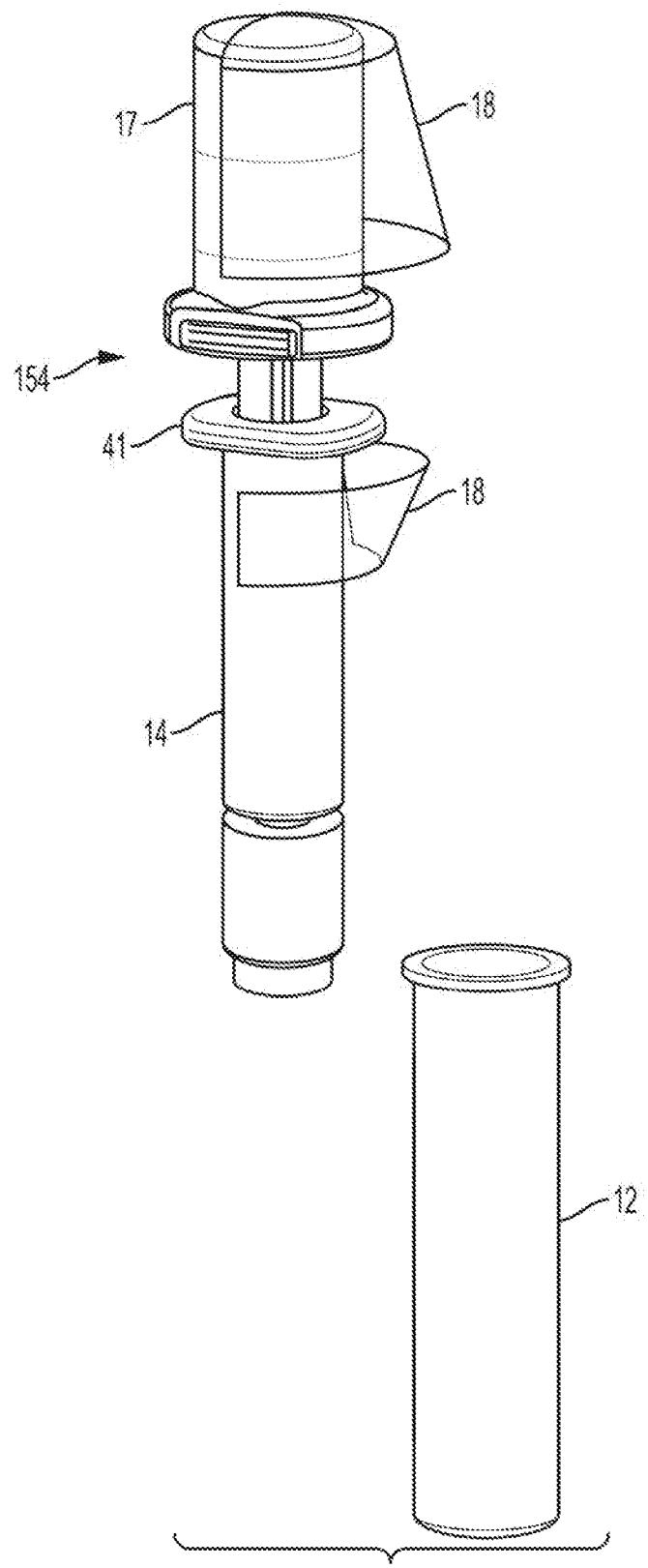
FIG. 19 is a perspective view of a syringe packaging system, with a film opened and a syringe removed from a tube in accordance with an embodiment of the present invention.
Figure 25:
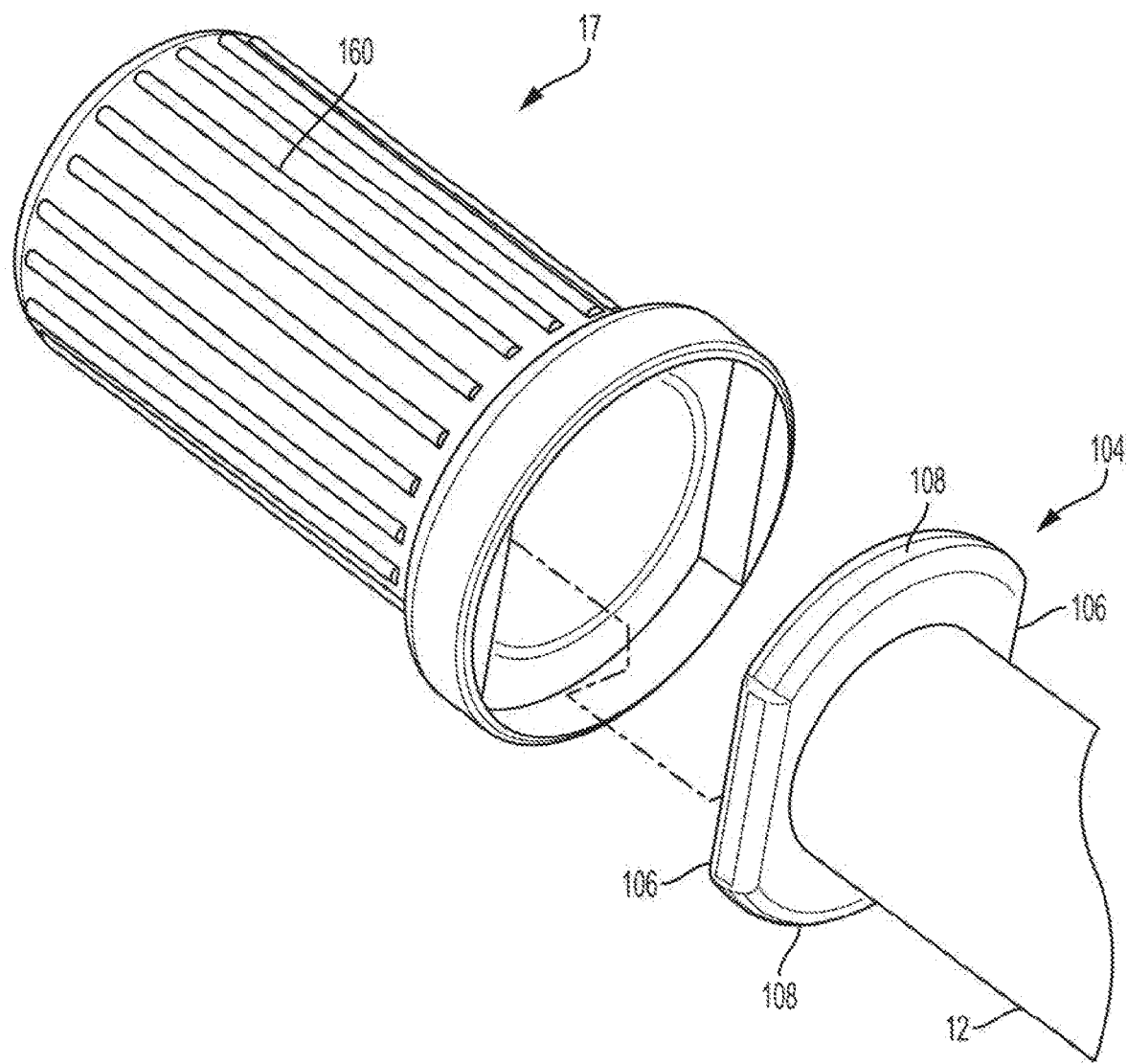
FIG. 25 is an exploded, perspective view of a cap and a tube in accordance with an embodiment of the present invention.
Figure 26:
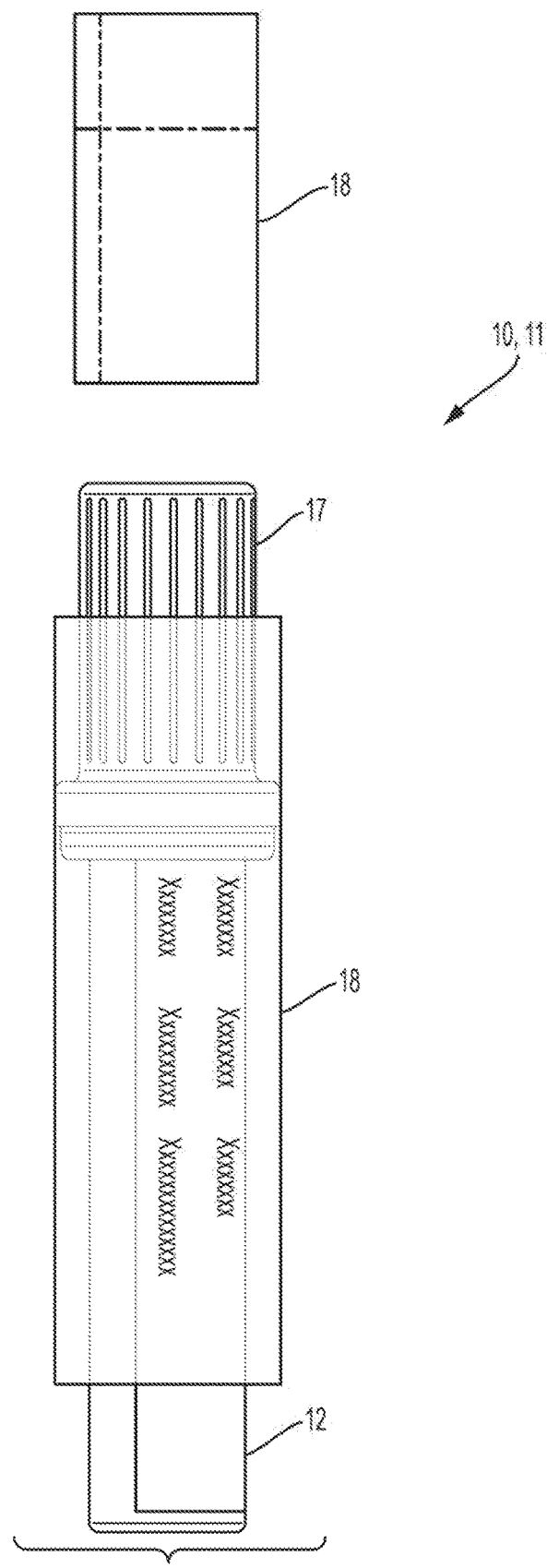
FIG. 26 is a front view of a syringe packaging system in accordance with an embodiment of the present invention.
Figure 27:
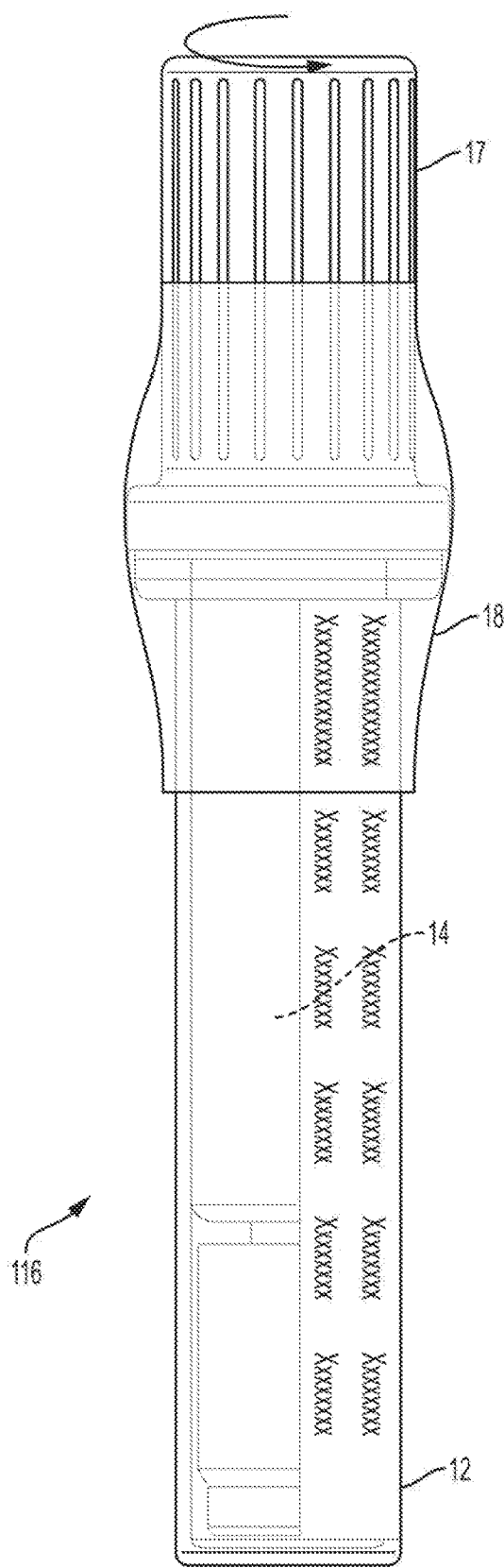
FIG. 27 is an elevation view of a viewing window of a syringe packaging system in accordance with an embodiment of the present invention.
Figure 28:
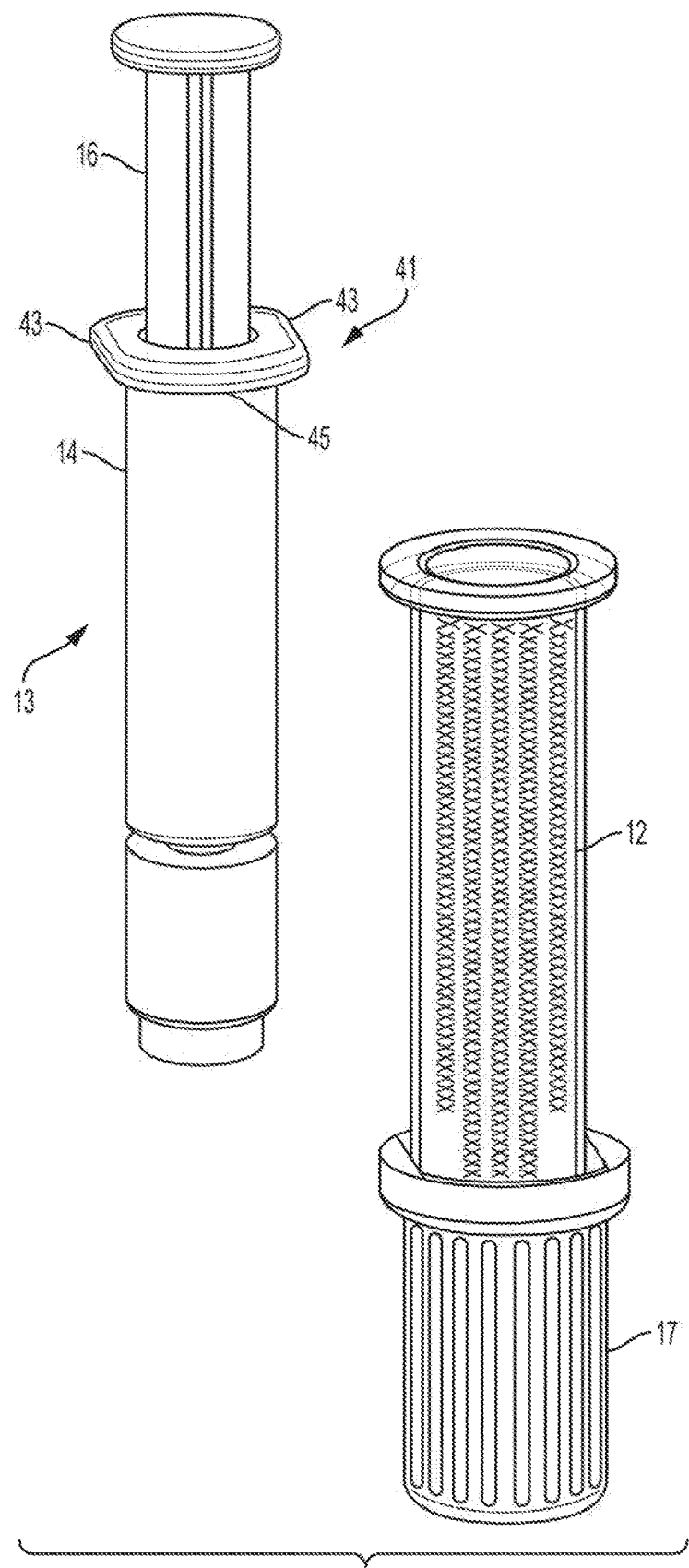
FIG. 28 is an exploded, perspective view of a syringe packaging system in accordance with an embodiment of the present invention.
Figure 29:
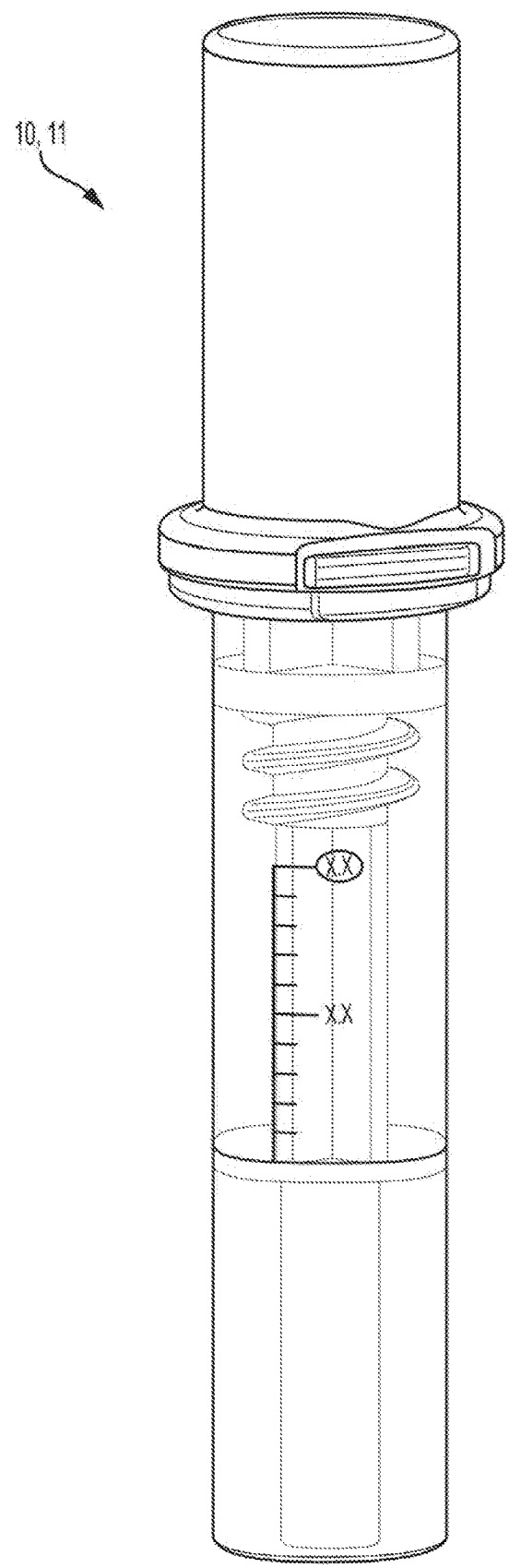
FIG. 29 is a perspective view of a syringe packaging system in accordance with an embodiment of the present invention.
Figure 30:
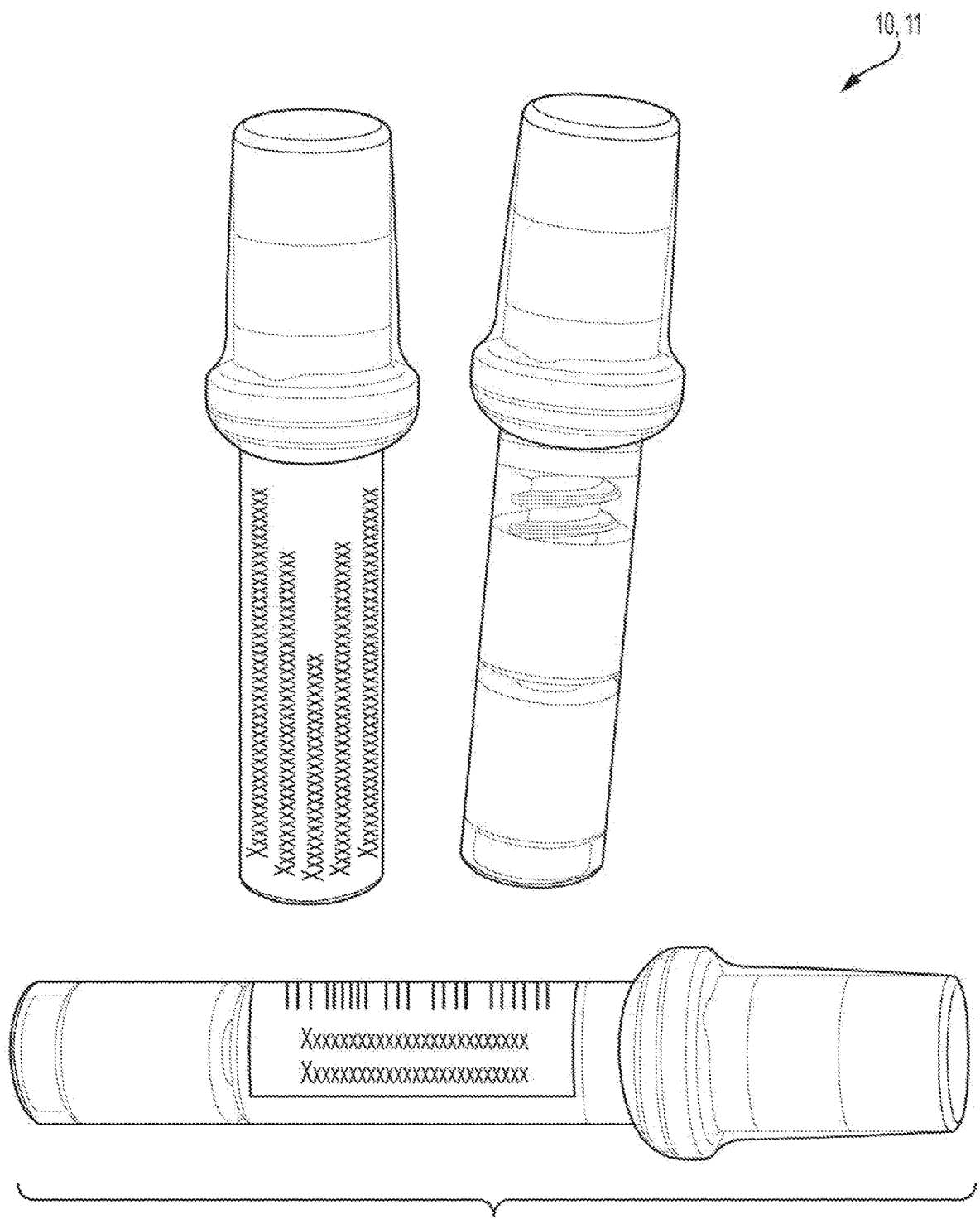
FIG. 30 is a perspective view of a plurality of syringe packaging systems in accordance with an embodiment of the present invention.

Referring to FIGS. 1-39, syringe barrel 14 generally includes a barrel body having a sidewall 30 extending between a first or distal end 32 and a second or proximal end 34. Sidewall 30 defines an elongate aperture or interior chamber 36 of syringe barrel 14. In one embodiment, interior chamber 36 may span the extent of syringe barrel 14 so that syringe barrel 14 is cannulated along its entire length. In one embodiment, syringe barrel 14 may be in the general form of an elongated cylindrical barrel as is known in the art in the general shape of a hypodermic syringe. In alternative embodiments, syringe barrel 14 may be in other forms for containing a fluid for delivery, such as in the general form of an elongated rectangular barrel, for example. Syringe barrel 14 may be formed of glass, or may be injection molded from thermoplastic material such as polypropylene and polyethylene according to techniques known to those of ordinary skill in the art, though it is to be appreciated that syringe barrel 14 may be made from other suitable materials and according to other applicable techniques. In certain configurations, syringe barrel 14 may include an outwardly extending flange 40 about at least a portion of proximal end 34. Flange 40 may be configured for easy grasping by a medical practitioner, as will be discussed herein. In one embodiment, flange 40 is a cut flange 41. Referring to FIG. 17, in one embodiment, the cut flange 41 includes a first flat wall portion 43 and a first arcuate wall portion 45.

Distal end 32 of syringe barrel 14 includes an outlet opening 38 (FIGS. 15 and 16) which is in fluid communication with chamber 36. Outlet opening 38 may be sized and adapted for engagement with a separate device, such as a needle assembly or IV connection assembly and, therefore, may include a mechanism for such engagement as is conventionally known. For example, distal end 32 may include a generally-tapered luer tip for engagement with an optional separate tapered luer structure of such a separate device for attachment therewith (not shown). In one configuration, both the tapered luer tip and the separate tapered luer structure may be provided with the syringe assembly 13. In such a configuration, the separate tapered luer structure may be fitted with an attachment mechanism, such as a threaded engagement, for corresponding engagement with a separate device (not shown). In another configuration, the tapered luer tip may be provided for direct engagement with a separate device (not shown). In addition, a mechanism for locking engagement therebetween may also be provided with at least one of the tapered luer tip and/or the separate tapered luer structure, such as a luer collar or luer lock including interior threads. Such luer connections and luer locking mechanisms are well known in the art.

Proximal end 34 of syringe barrel 14 is generally open-ended, but is intended to be closed off to the external environment as discussed herein. Syringe barrel 14 may also include markings, such as graduations located on sidewall 30, for providing an indication as to the level or amount of fluid contained within interior chamber 36 of syringe barrel 14. Such markings may be provided on an external surface of sidewall 30, an internal surface of sidewall 30, or integrally formed or otherwise within sidewall 30 of syringe barrel 14. In other embodiments, alternatively, or in addition thereto, the markings may also provide a description of the contents of the syringe or other identifying information as may be known in the art, such as maximum and/or minimum fill lines.

Syringe barrel 14 may be useful as a pre-filled syringe, and, therefore, may be provided for end use with a fluid F (FIG. 16), such as a medication or drug, contained within interior chamber 36 of syringe barrel 14, pre-filled by the manufacturer. In this manner, syringe barrel 14 can be manufactured, pre-filled with a medication, sterilized, and packaged in appropriate packaging such as tube 12 and cap 17 for delivery, storage, and use by the end user, without the need for the end user to fill the syringe with medication from a separate vial prior to use. In one embodiment, syringe barrel 14 may include a tip cap or sealing cap member 42 including a seal 44 disposed at distal end 32 of syringe barrel 14 to seal a fluid F, such as a medication, within interior chamber 36 of syringe barrel 14. In one embodiment, seal 44 may be formed of a pierceable elastomer material.

As used herein, the term "drug" and/or "medication" refers to a pharmaceutically active ingredient(s) and any pharmaceutical liquid composition containing the pharmaceutically active ingredient(s). Pharmaceutical liquid compositions include forms such as solutions, suspensions, emulsions, and the like. These pharmaceutical liquid compositions can be administered orally or by injection.

Referring to FIGS. 15 and 16, syringe assembly 13 includes stopper 19 which is moveably or slidably disposed within interior chamber 36 of syringe barrel 14, and in sealing contact with the internal surface of sidewall 30 of syringe barrel 14. Stopper 19 is sized relative to syringe barrel 14 to provide sealing engagement with the interior surface of sidewall 30 of syringe barrel 14. Additionally, stopper 19 may include one or more annular ribs extending around the periphery of stopper 19 to increase the sealing engagement between stopper 19 and the interior surface of sidewall 30 of syringe barrel 14. In alternate embodiments, a singular O-ring or a plurality of O-rings may be circumferentially disposed about stopper 19 to increase the sealing engagement with the interior surface of sidewall 30 of syringe barrel 14.

Figure 13:
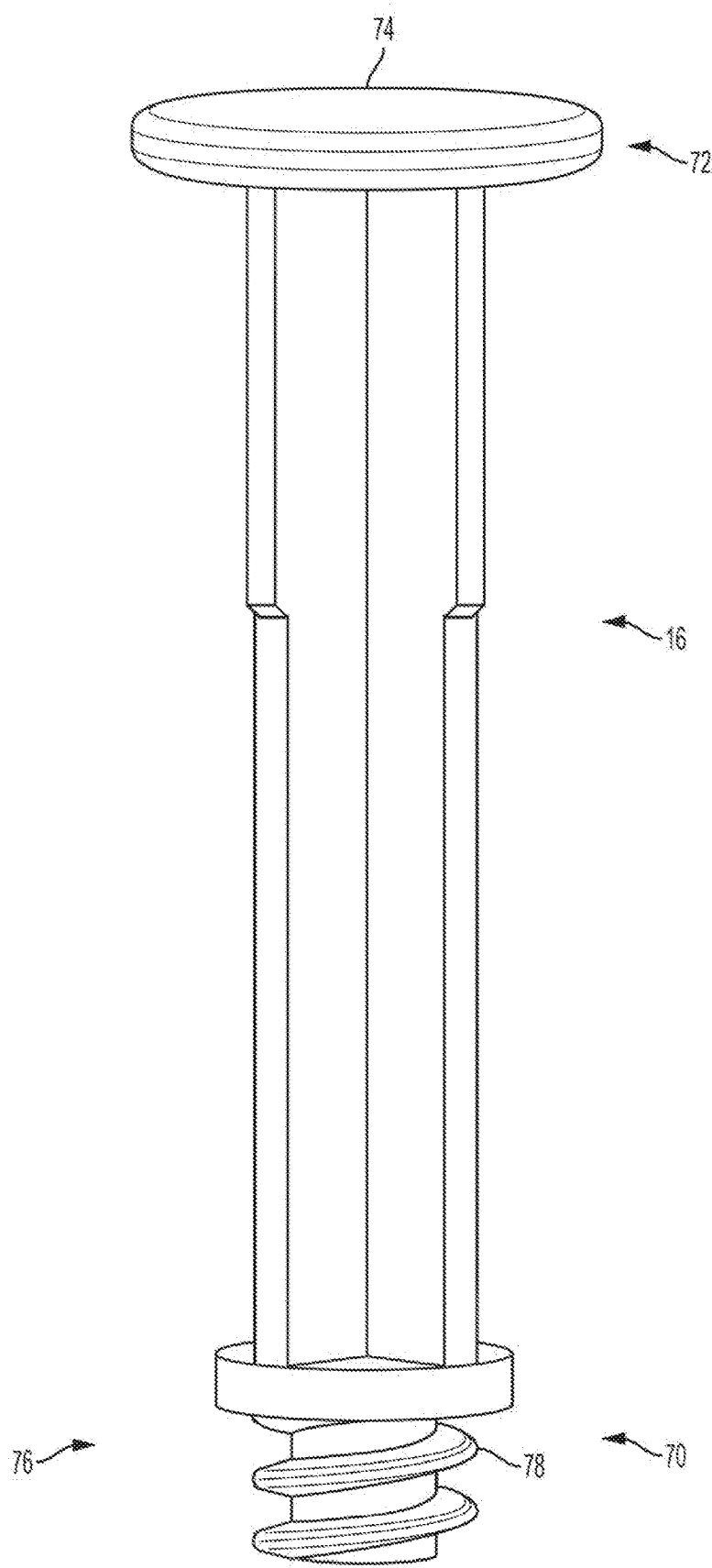
FIG. 13 is a perspective view of a plunger rod in accordance with an embodiment of the present invention.
Figure 14:
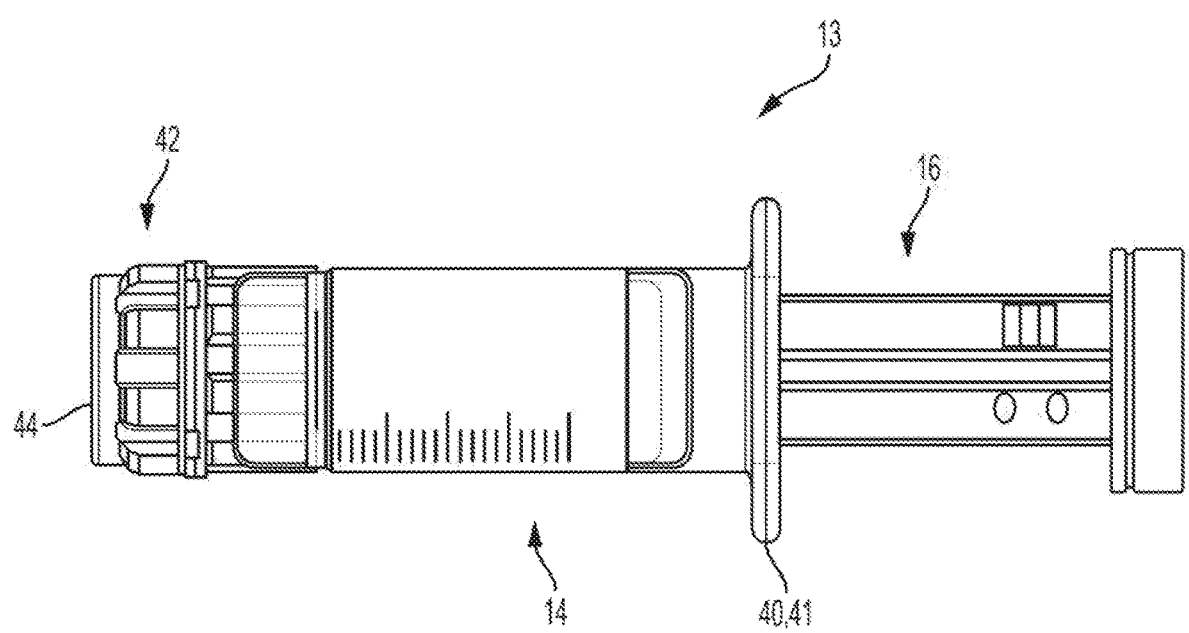
FIG. 14 is an elevation view of a syringe in accordance with an embodiment of the present invention.

Referring to FIG. 13, in one embodiment, stopper 19 includes a first or distal end 50 and a second or proximal end 52 defining a plunger receiving aperture 54 formed therein and having a securement feature or engagement portion 56 for securing plunger rod 16 to stopper 19. In one embodiment, referring to FIG. 13, the engagement portion 56 may include a threaded portion 58.

Referring to FIG. 13, syringe assembly 13 further includes plunger rod 16 which provides a mechanism for dispensing fluid contained within interior chamber 36 of syringe barrel 14 through outlet opening 38 upon connection of plunger rod 16 to syringe barrel 14 via stopper 19 as will be described in more detail below. Plunger rod 16 is adapted for advancing stopper 19. For example, the plunger rod 16 is able to advance stopper 19 between the positions shown in FIGS. 15 and 16. In one embodiment, plunger rod 16 is sized for movement within interior chamber 36 of syringe barrel 14, and generally includes a first or distal end 70, a second or proximal end 72, a flange 74 disposed adjacent second end 72, and a securement feature or engagement portion 76 for securing plunger rod 16 to stopper 19. In one embodiment, referring to FIGS. 15 and 16, the engagement portion 76 of plunger rod 16 may include a threaded portion 78. In one embodiment, the flange 74 forms a thumb pad for a user to manipulate the plunger rod 16. In one embodiment, the engagement portion 76 is disposed adjacent the first end 70.

In one embodiment, plunger rod 16 can be secured to stopper 19 by threadingly engaging threaded portion 58 of stopper 19 to threaded portion 78 of plunger rod 16 as shown in FIGS. 15 and 16. In other embodiments, plunger rod 16 can be secured to stopper 19 using a snap fit mechanism, a ball detent, locking tabs, spring loaded locking mechanism, latch, adhesive, or other similar mechanism. In all embodiments, plunger rod 16 is locked, secured, or engaged to stopper 19, i.e., significant relative movement between plunger rod 16 and stopper 19 is prevented.

In some embodiments, plunger rod 16 and stopper 19 may be co-formed such as by co-extrusion. In other embodiments, plunger rod 16 and stopper 19 may be integrally formed as a plunger/stopper assembly.

Referring to FIGS. 11 and 12, in one embodiment, the length of a plunger rod 16 of the present disclosure (FIG. 12) is shorter than the length of a conventional or standard plunger rod 200 (FIG. 11). In this manner, a plunger rod 16 of the present disclosure allows for reduced storage space of a pre-filled syringe.

Additionally, at the end of the injection, when the entire drug has been delivered, the thumb pad or flange 74 of the plunger rod 16 of the present disclosure is much closer to the flange 40 of the syringe barrel 14 than a standard syringe is. For example, in one embodiment, the distance between an upper surface of the flange 40 of the syringe barrel 14 and a lower surface of the flange 74 of the plunger rod 16 may be between 0.5 to 2.5 mm. In another embodiment, the distance between an upper surface of the flange 40 of the syringe barrel 14 and a lower surface of the flange 74 of the plunger rod 16 may be between 0.9 to 2.3 mm. In another embodiment, the distance between an upper surface of the flange 40 of the syringe barrel 14 and a lower surface of the flange 74 of the plunger rod 16 may be around 1.6 mm. In this manner, the global length of a prefilled syringe is reduced, leading to a smaller required space for storage.

Figure 5:
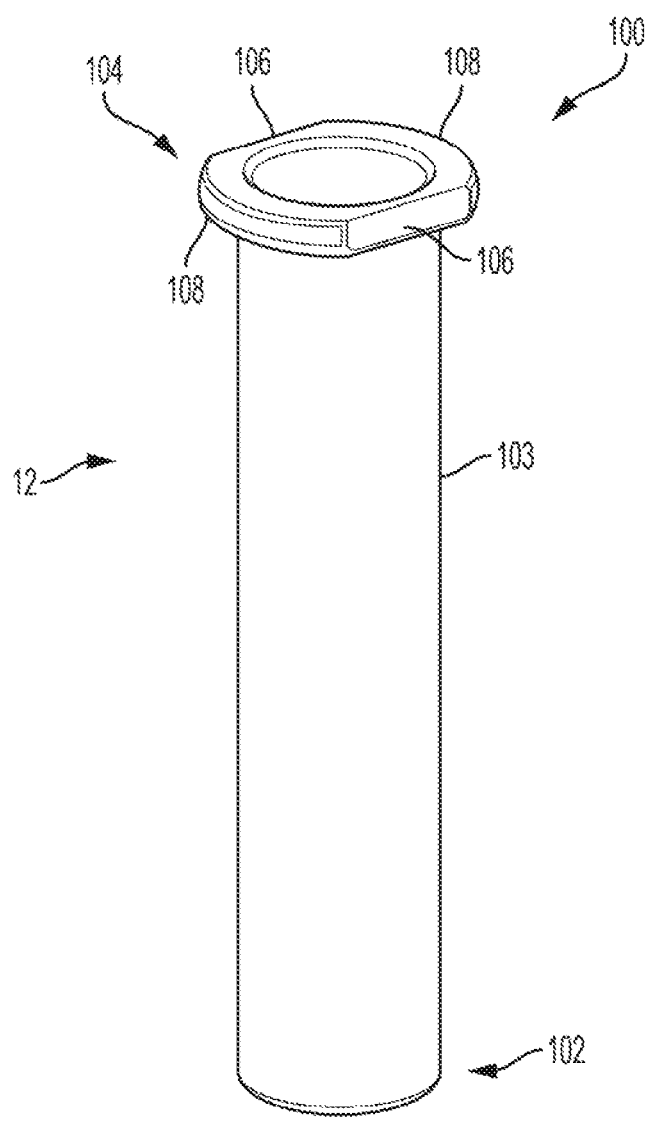
FIG. 5 is a perspective view of a tube in accordance with an embodiment of the present invention.
Figure 6:
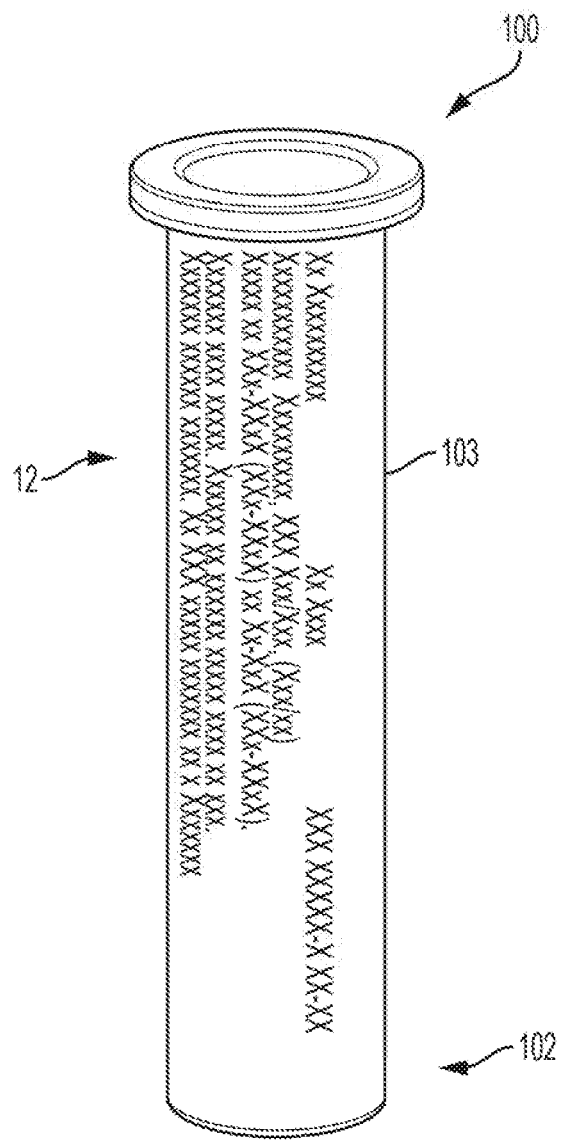
FIG. 6 is a perspective view of a tube with a label in accordance with an embodiment of the present invention.
Figure 7:
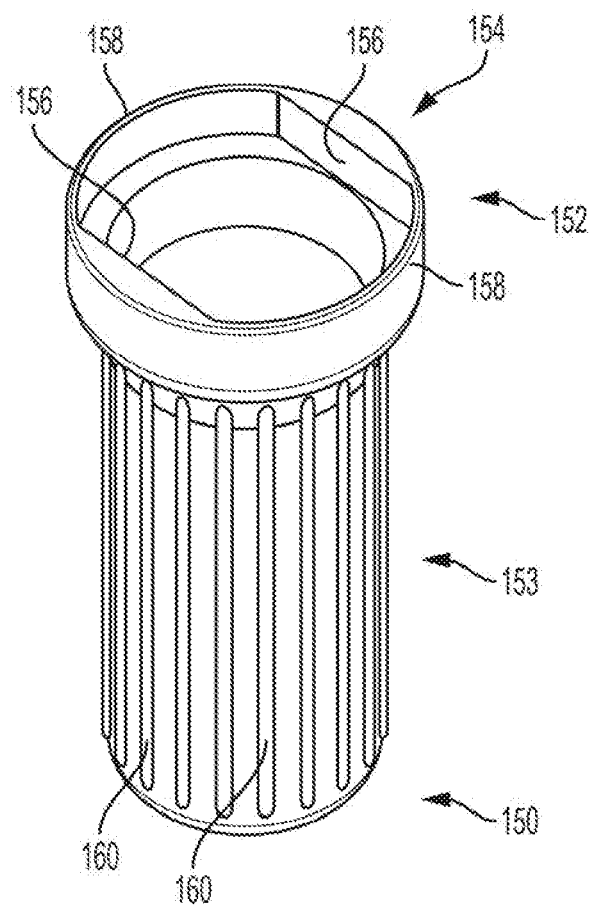
FIG. 7 is a perspective view of a cap in accordance with an embodiment of the present invention.
Figure 8:
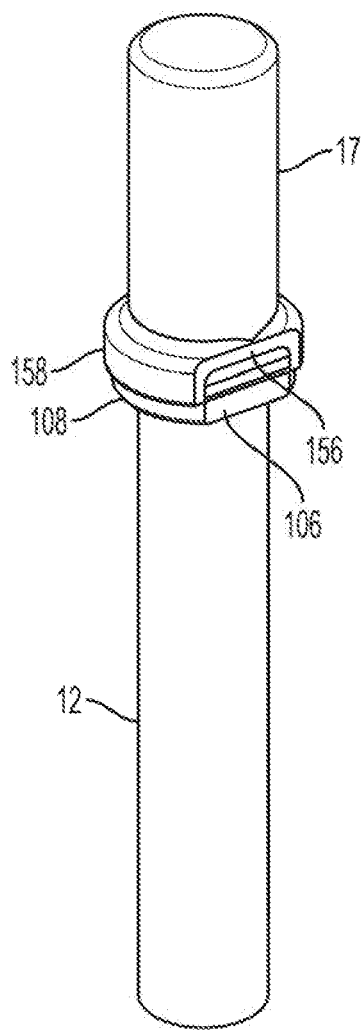
FIG. 8 is a perspective view of a packaging member in accordance with an embodiment of the present invention.
Figure 9:
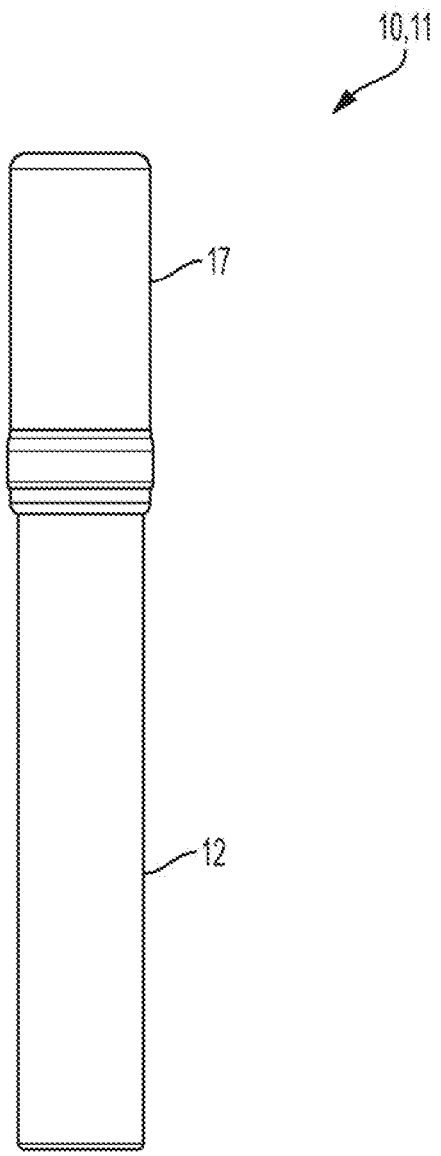
FIG. 9 is an elevation view of a packaging member in accordance with an embodiment of the present invention.
Figure 10:
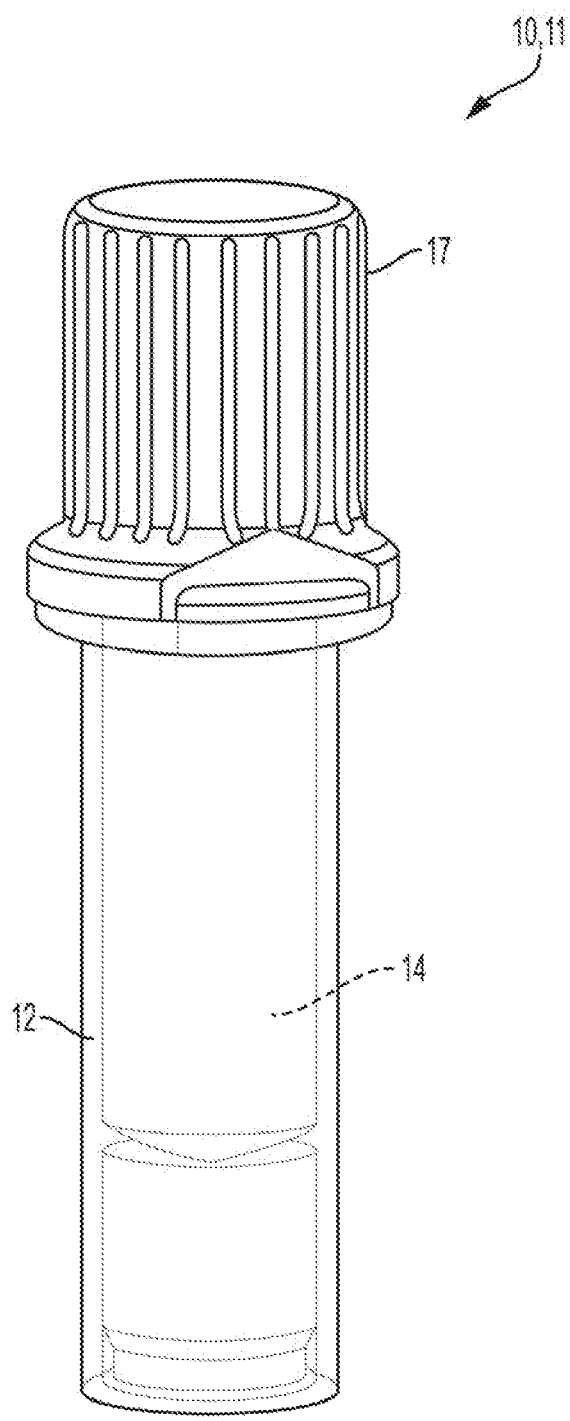
FIG. 10 is a perspective view of a packaging member in accordance with another embodiment of the present invention.

Referring to FIG. 5, a tube 12 of the present disclosure encloses the syringe barrel 14 and includes a proximal end 100, a distal end 102, and a sidewall 103 extending therebetween. In one embodiment, the proximal end 100 of the tube 12 includes a tube cut flange 104. In one embodiment, the tube cut flange 104 includes a second flat wall portion 106 and a second arcuate wall portion 108. The distal end 102 of the tube 12 is closed. The tube 12 of the present invention provides a mechanical protection of the syringe barrel 14 that is contained inside. The tube 12 also provides a good support for labeling.

Referring to FIGS. 1-3, 8, and 9, with the syringe barrel 14 contained within the tube 12, the cut flange 41 of the syringe barrel 14 is aligned with the tube cut flange 104. For example, the first flat wall portion 43 of the cut flange 41 of the syringe barrel 14 is aligned with the second flat wall portion 106 of the tube 12 and the first arcuate wall portion 45 of the cut flange 41 of the syringe barrel 14 is aligned with the second arcuate wall portion 108 of the tube 12. The alignment of the cut flange 41 of the syringe barrel 14 with the tube cut flange 104 of the tube 12 minimizes the global size of the packaging of the present disclosure.

The tube 12 of the present disclosure provides mechanical protection of the syringe barrel 14 and the flange 40, 41 of the syringe barrel 14 with the flange 40, 41 of the syringe barrel 14 being supported by the tube cut flange 104 of the tube 12.

In one embodiment, the tube 12 may be formed of a plastic material. For example, the tube 12 may be formed of polyethylene terephthalate (PET), polypropylene (PP), polycarbonate (PC), or other material. In one embodiment, the tube 12 is formed of a transparent material. In this manner, referring to FIG. 27, a portion of the tube 12 forms a viewing window 116 that allows a user to see data and/or information written on an outer surface of the syringe barrel 14. Thus, the tube 12 of the present disclosure provides access to the essential data/information that is written on a surface of the syringe barrel 14 placed inside the tube 12, as well as the tube 12 provides visual access to the contents of the syringe barrel 14. In other embodiments, the color, transparency and/or other attributes of the tube material may be selected based on, for example, a characteristic, such as the UV sensitivity, of the drug contained inside the syringe. Additionally, the color and/or other attributes of the tube material may be selected based on a desired color coding scheme for the syringe packaging or other labeling considerations.

The closed distal end 102 of the tube 12 acts as a barrier to avoid any piercing and/or withdrawal of a drug contained inside the syringe 13 through a seal 44 of the pre-filled syringe 13, with a needle, for example. In this manner, with the syringe barrel 14 enclosed within the tube 12, the closed distal end 102 of the tube 12 shields the distal end 32 and the seal 44 of the syringe barrel 14. The tube 12 prevents any piercing of the syringe barrel 14 and avoids any withdrawal of a drug contained inside the syringe barrel 14.

In one embodiment, the thickness of the flange 104 of the tube 12 is between 1 mm and 3 mm. In this manner, the thickness of the flange 104 of the tube 12 prevents the tube 12 from passing under or being removed from the film 18 in the final packaging. For example, if someone tries to pull on the tube 12 in a distal direction to slide the tube 12 under the film 18.

Referring to FIGS. 1-10 and 17-19, a cap 17 of the present disclosure, along with the tube 12, encloses the syringe 13. In one embodiment, the cap 17 includes a first end 150, a second end 152, and a sidewall 153 extending therebetween. The second end 152 includes a cut skirt 154.

In one embodiment, the cut skirt 154 includes a third flat wall portion 156 and a third arcuate wall portion 158. With the pre-filled syringe 13 enclosed within the packaging member 11, the cut skirt 154 of the cap 17 surrounds the cut flange 41 of the syringe barrel 14. The tube 12 and the cap 17 of the present disclosure provides mechanical protection of the syringe 13 and the flange 40, 41 of the syringe barrel 14 with the flange 40, 41 of the syringe barrel 14 being supported by the tube cut flange 104 of the tube 12 and surrounded by the cut skirt 154 of the cap 17.

The cut skirt 154 of the cap 17 provides mechanical protection of the plunger rod 16 and of the flange 40, 41 of the syringe barrel 14. The cut skirt 154 of the cap 17 also prevents any access to the stopper 19 and/or other areas of the syringe 13, thereby preventing any potential of undesired drug withdrawal from the syringe 13.

In one embodiment, as described above, the cut skirt 154 of the cap 17 surrounds the flange 104 of the tube 12. In such embodiments, the flange 40, 41 of the syringe barrel 14 is not visible and is also not accessible.

Referring to FIG. 17, in one embodiment, the skirt 154 is cut to have the same shape as the flange 104 of the tube 12. The tube 12 is able to perfectly fit with the cap 17 and the cut parts are aligned and the global size is optimized. For example, the cut skirt 154 of the cap 17 is aligned with the cut flange 104 of the tube 12. The alignment of the cut skirt 154 of the cap 17 with the tube cut flange 104 of the tube 12 minimizes the global size of the packaging of the present disclosure. Furthermore, the cut skirt 154 of the cap 17 protects the flange 40, 41 of the syringe barrel 14 which is not accessible.

In one embodiment, the surface of the cap 17 is an ideal area to stick an adhesive label with the information required for such a device and the drugs contained inside the syringe 13.

In one embodiment, the cap 17 has an easy grip surface with longitudinal ribs 160. In other embodiments, the cap 17 can have other surfaces, for example, a flat surface.

In one embodiment, the cap 17 may be formed of a plastic material. For example, the cap 17 may be formed of an opaque material, polyethylene terephthalate (PET), polypropylene (PP), polycarbonate (PC), or other material.

Referring to FIGS. 1-4 and 17-19, the packaging member 11 includes a film 18 that is securable to a portion of the tube 12 and a portion of the cap 17 to connect the tube 12 and the cap 17 with the pre-filled syringe 13 enclosed within the cap 17 and the tube 12. In this manner, the film 18, together with the tube 12 and the cap 17, provides protection of the syringe 13, reduces the global size of the packaging, and allows for easy storage in a storage unit.

In one embodiment, the film 18 comprises a shrinkable film. The film 18 can include a tamper evident sleeve.

The film 18 of the present disclosure is used as a tamper evidence feature. Additionally, the film 18 of the present disclosure maintains together and connects the tube 12 and the cap 17. Furthermore, the film 18 of the present disclosure also provides proof of the package integrity maintenance.

In one embodiment, the film 18 includes circular pre-cut perforations 28 to facilitate the opening of the film 18 and the removal of the syringe 13 from the packaging assembly 11.

In some embodiments, the tamper evidence features may include breaking tabs that connect a ring to the skirt 154 of the cap 17. In such embodiments, the ring can be positioned under the flange 104 of the tube 12 and remain at this position after the breakage of the tabs leading to the opening of the packaging.

All of the components of syringe packaging system 10 may be constructed of any known material, and are desirably constructed of medical-grade polymers.

In some embodiments, the syringe packaging system 10 is configured to protect the prefilled syringe from environmental factors that may negatively impact the stability of the medication or drug contained within interior chamber 36, such as ultraviolet (UV) radiation, moisture, and/or oxygen. This may be achieved by selecting a material for the tube, cap, and/or shrink wrap sleeve having a desired property. In some embodiments, the tube and/or cap are constructed of medical-grade polymers having a low oxygen permeability and/or UV barrier property. In certain embodiments, the tube and cap are assembled by welding to further reduce ingress of undesirable environmental factors. Materials having low oxygen, moisture, and/or UV permeation properties are known to those of ordinary skill in the art.

Referring to FIGS. 1-39, packaging of a syringe 13 within packaging assembly 11 will now be described. Initially, syringe barrel 14, plunger rod 16, tube 12, and cap 17 are sterilized according to techniques known to those of ordinary skill in the art. In some embodiments, syringe barrel 14 may be pre-filled as described above.

Next, a plunger rod 16 of the present disclosure can be connected to the syringe 13 via engagement of the securement feature 76 of the plunger rod 16 with the engagement portion 56 of the stopper 19 as shown in FIGS. 15 and 16. Referring to FIGS. 1-3 and 17, the syringe 13 can be loaded within the tube 12 such that the closed distal end 102 of the tube 12 shields the distal end 32 of the syringe barrel 14. The tube 12 of the present disclosure provides mechanical protection of the syringe barrel 14 and the flange 40, 41 of the syringe barrel 14 with the flange 40, 41 of the syringe barrel 14 being supported by the tube cut flange 104 of the tube 12.

Next, the cap 17 is positioned over the plunger rod 16 and in engagement with the tube 12 as described above. For example, with the pre-filled syringe 13 enclosed within the packaging member 11, the cut skirt 154 of the cap 17 surrounds the cut flange 41 of the syringe barrel 14. The tube 12 and the cap 17 of the present disclosure provides mechanical protection of the syringe 13 and the flange 40, 41 of the syringe barrel 14 with the flange 40, 41 of the syringe barrel 14 being supported by the tube cut flange 104 of the tube 12 and surrounded by the cut skirt 154 of the cap 17.

Figure 2:
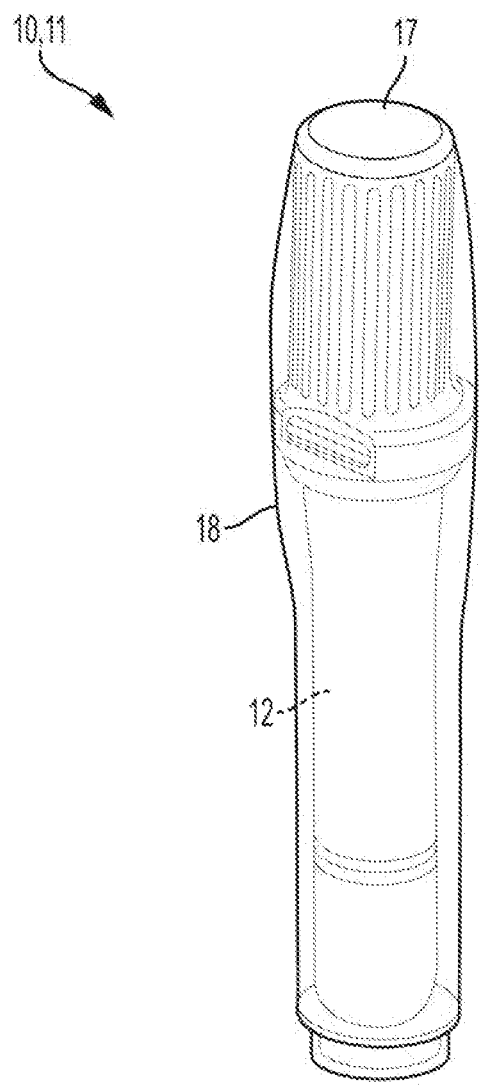
FIG. 2 is a perspective view of a syringe packaging system in accordance with another embodiment of the present invention.
Figure 3:
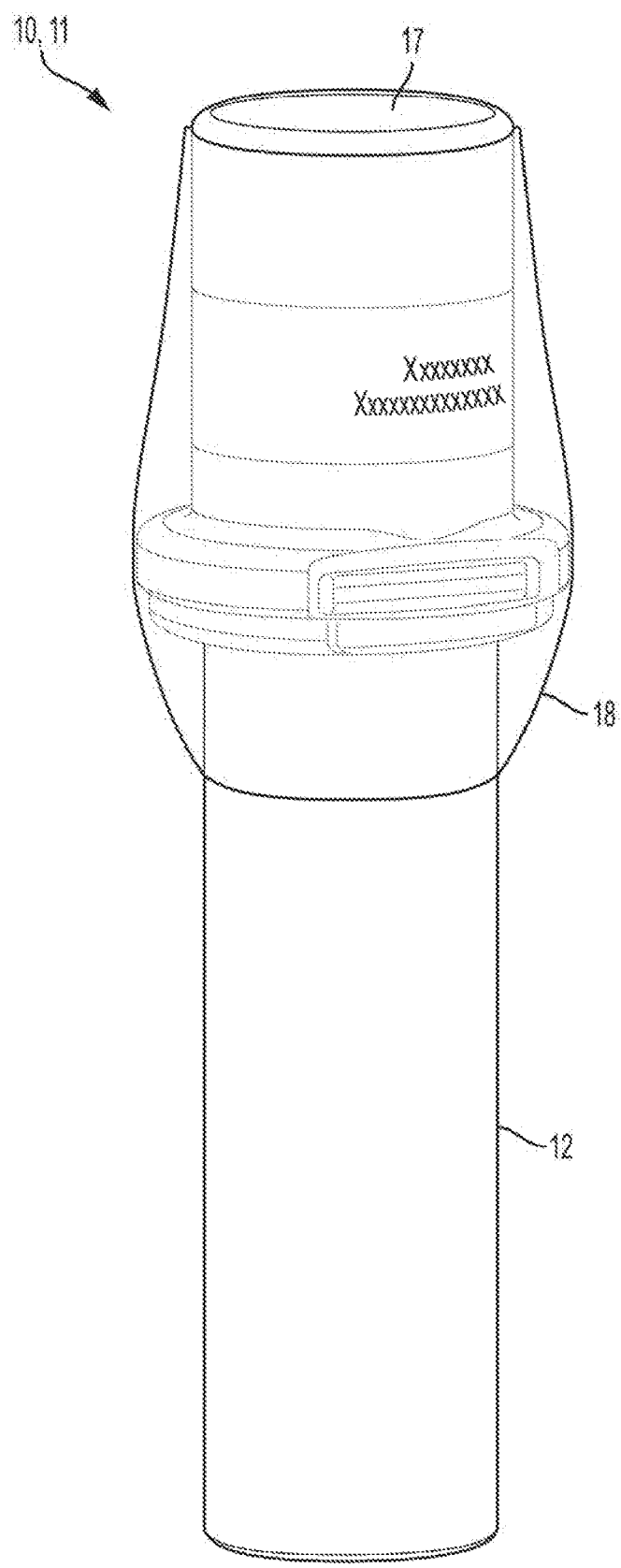
FIG. 3 is a perspective view of a syringe packaging system in accordance with another embodiment of the present invention.
Figure 4:
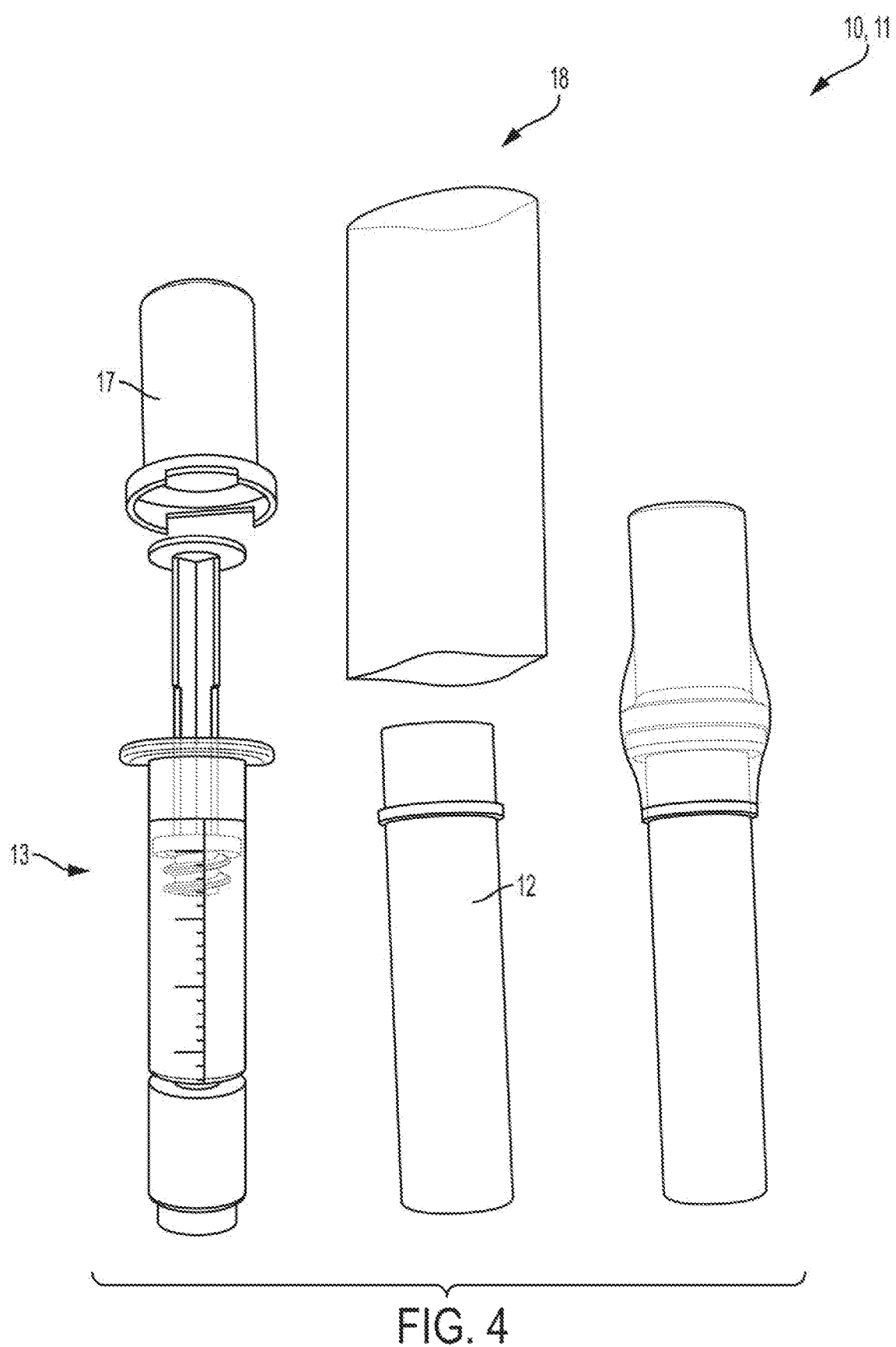
FIG. 4 is an exploded, perspective view of a syringe packaging system in accordance with an embodiment of the present invention.
Figure 31:
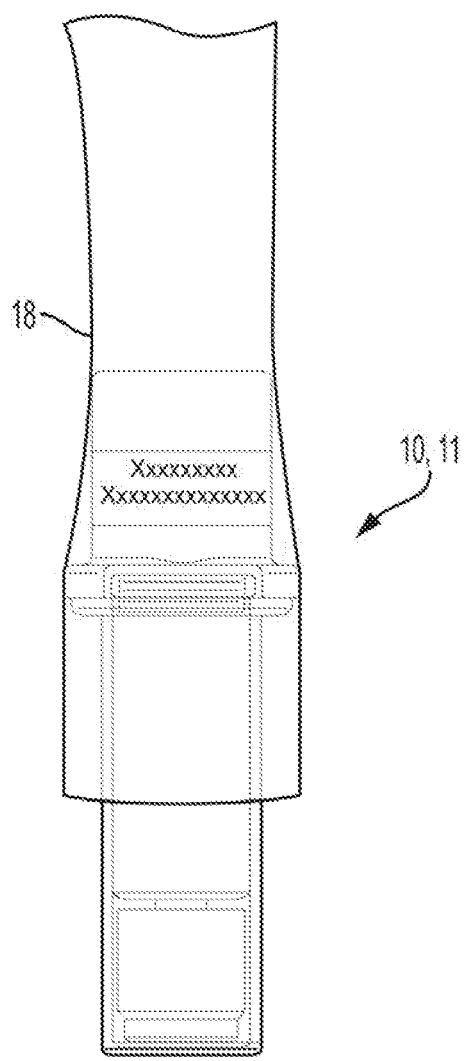
FIG. 31 is a perspective view of a syringe packaging system in accordance with another embodiment of the present invention.

Next, the film 18 is secured to a portion of the tube 12 and a portion of the cap 17 to connect the tube 12 and the cap 17 with the pre-filled syringe 13 enclosed within the cap 17 and the tube 12. Referring to FIGS. 1 and 3, in some embodiments, the film 18 covers a portion of the tube 12 and a portion of the cap 17. Referring to FIGS. 2 and 31, in other embodiments, the film 18 is able to cover a larger portion of the tube 12 and/or a larger portion of the cap 17.

Referring to FIGS. 32-39, a process of removing a syringe 13 from the packaging assembly 11 of the present disclosure will now be described.

Figure 32:
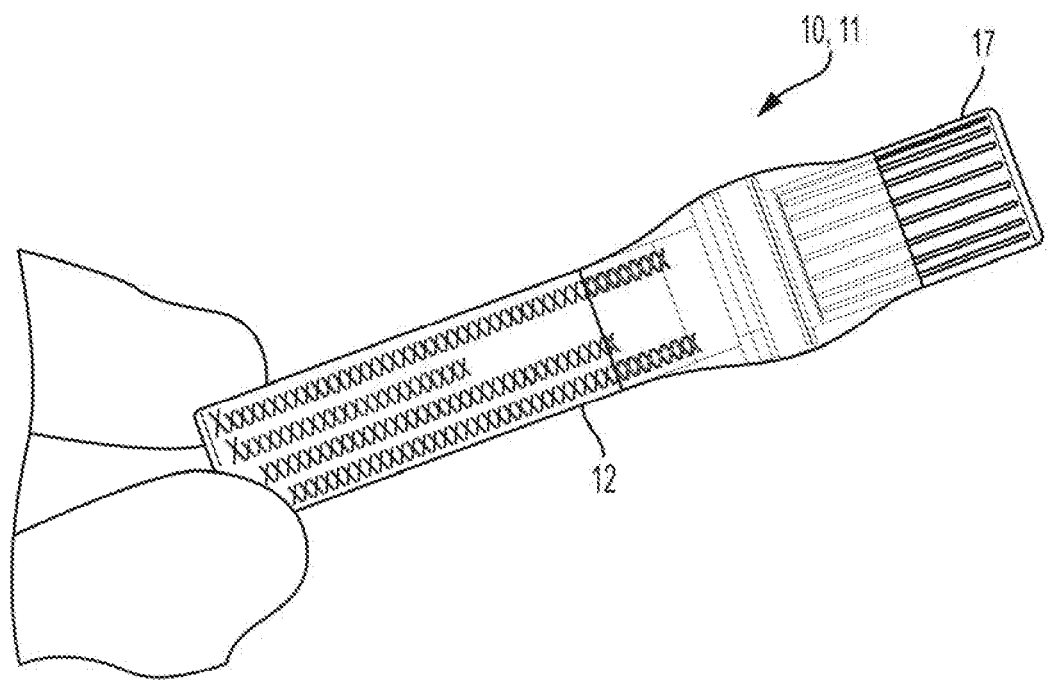
FIG. 32 is a perspective view of a first step of using a device of the present disclosure in accordance with an embodiment of the present invention.

Referring to FIG. 32, when a user desires to remove the syringe 13 from the packaging assembly 11, a user may inspect the packaging assembly 11 by verifying: (1) the tube and cap integrity; (2) the tamper evident sleeve integrity; and (3) if the tamper evident sleeve has been damaged, the syringe 13 is not used.

Figure 33:
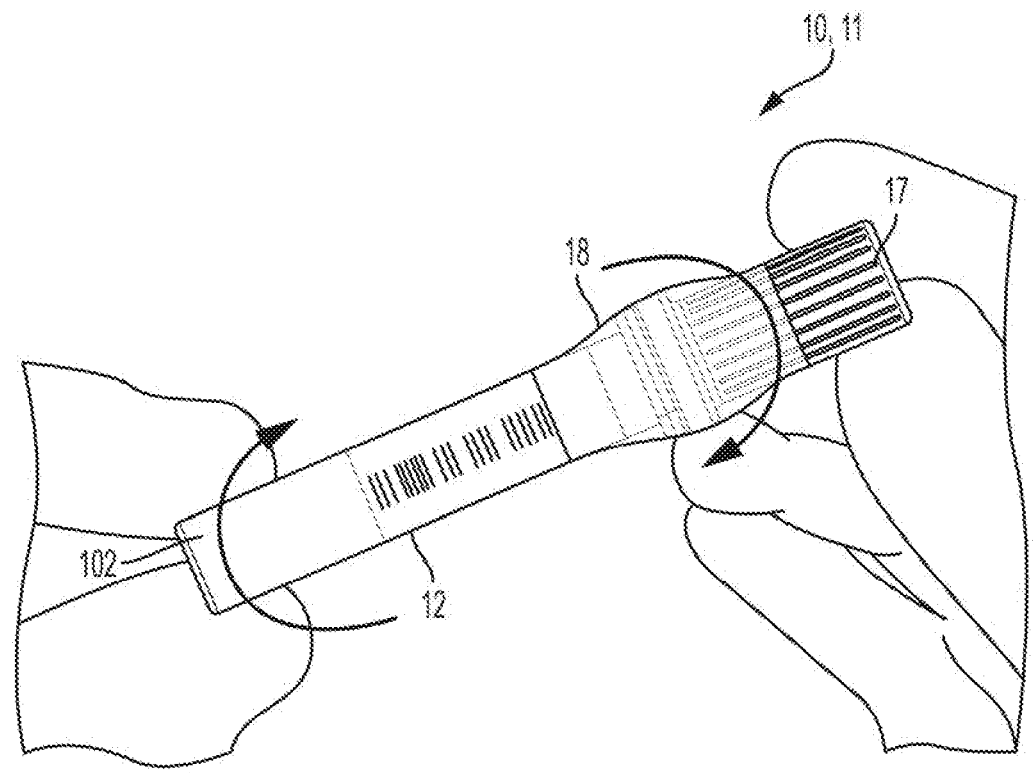
FIG. 33 is a perspective view of a second step of using a device of the present disclosure in accordance with an embodiment of the present invention.
Figure 34:
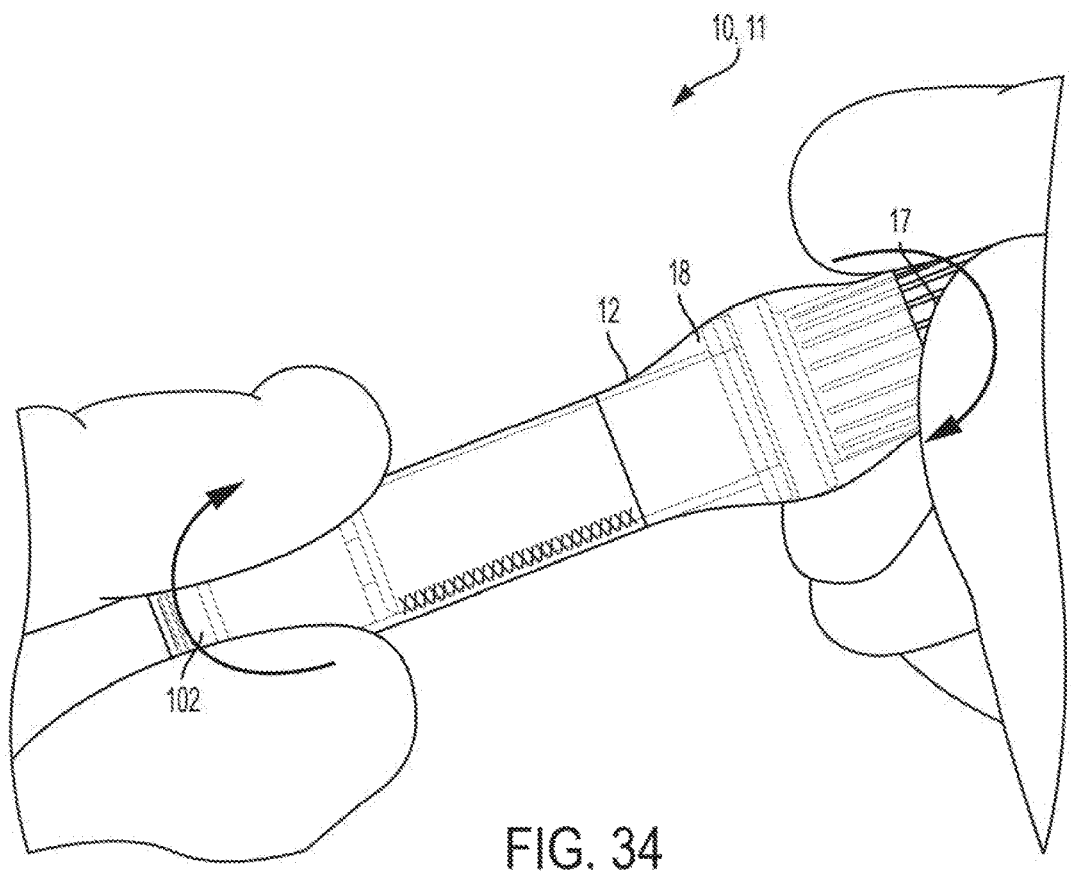
FIG. 34 is a perspective view of a third step of using a device of the present disclosure in accordance with an embodiment of the present invention.

Referring to FIGS. 33 and 34, to visualize a bar code and/or any other relevant information and inspect the contents of the syringe prior to opening, the lower end 102 of the tube 12 may be held and the cap 17 rotated relative to the tube 12 to visualize. For example, referring to FIG. 27, a portion of the tube 12 forms a viewing window 116 that allows a user to see data and/or information written on an outer surface of the syringe barrel 14. Thus, the tube 12 of the present disclosure provides access to the essential data/information that is written on a surface of the syringe barrel 14 placed inside the tube 12, as well as the tube 12 provides visual access to the contents of the syringe barrel 14.

Figure 35:
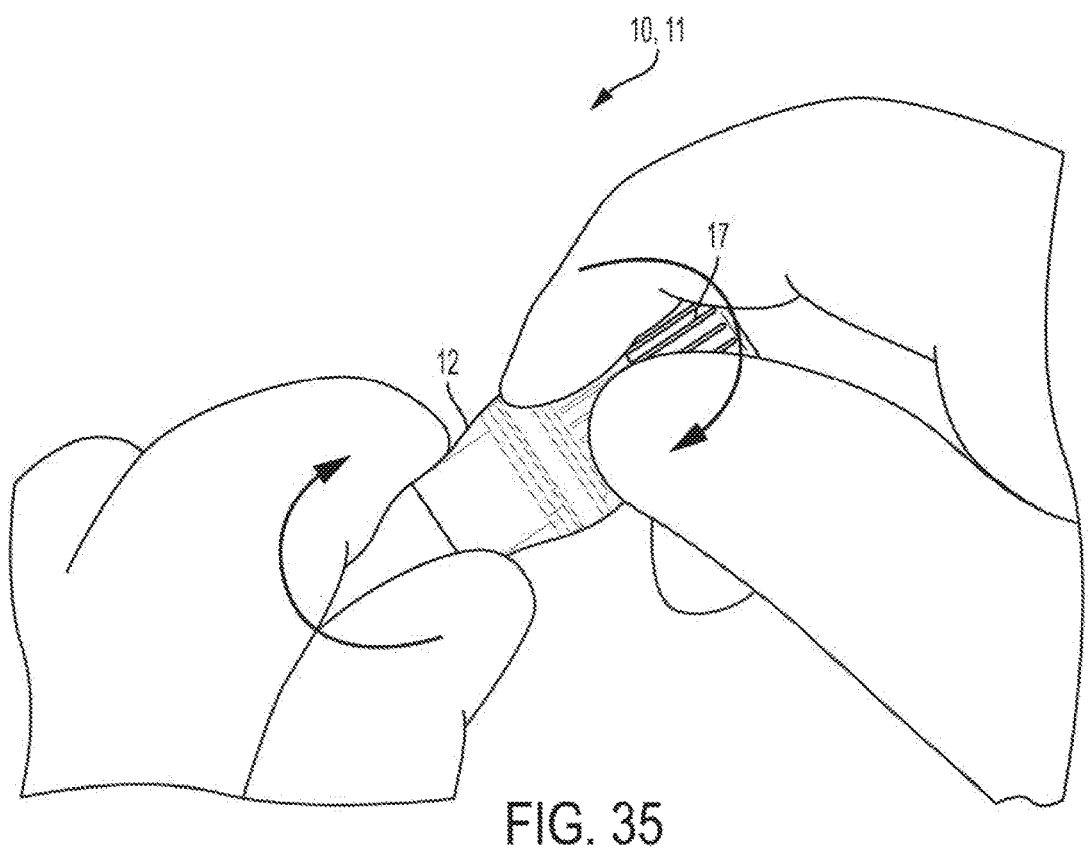
FIG. 35 is a perspective view of a fourth step of using a device of the present disclosure in accordance with an embodiment of the present invention.

Referring to FIG. 35, to open the packaging assembly 11, the cap 17 and the tube 12 are held, grasping the tamper evident sleeve, on either side of the syringe flange. Next, the film 18 can be twisted until the tamper evident sleeve breaks and the cap 17 and the tube 12 separate.

Figure 36:
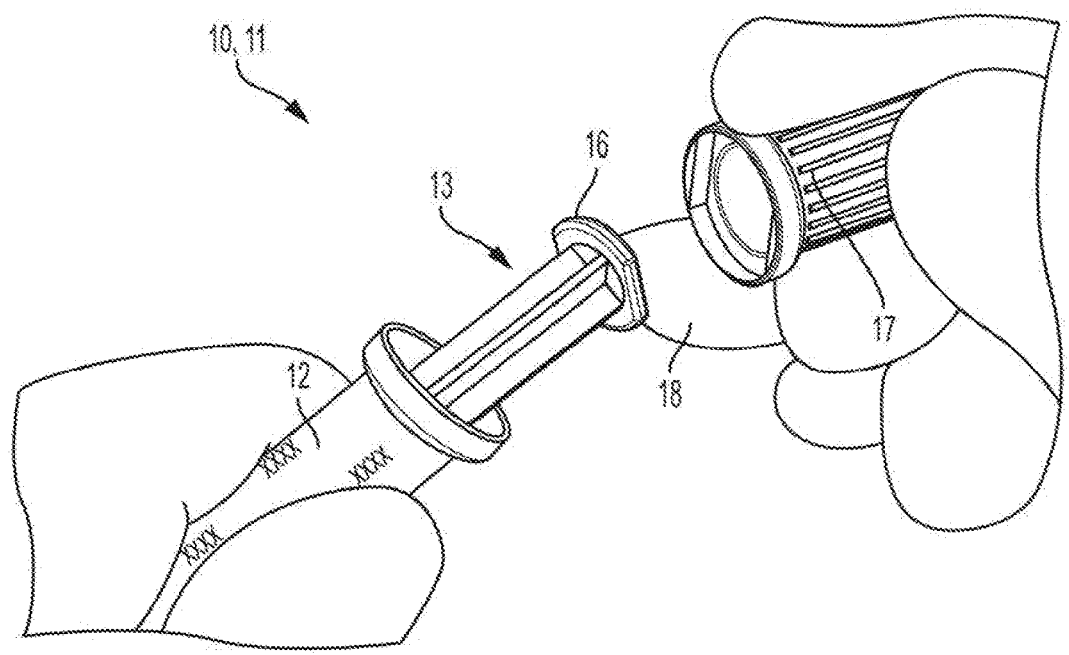
FIG. 36 is a perspective view of a fifth step of using a device of the present disclosure in accordance with an embodiment of the present invention.
Figure 37:
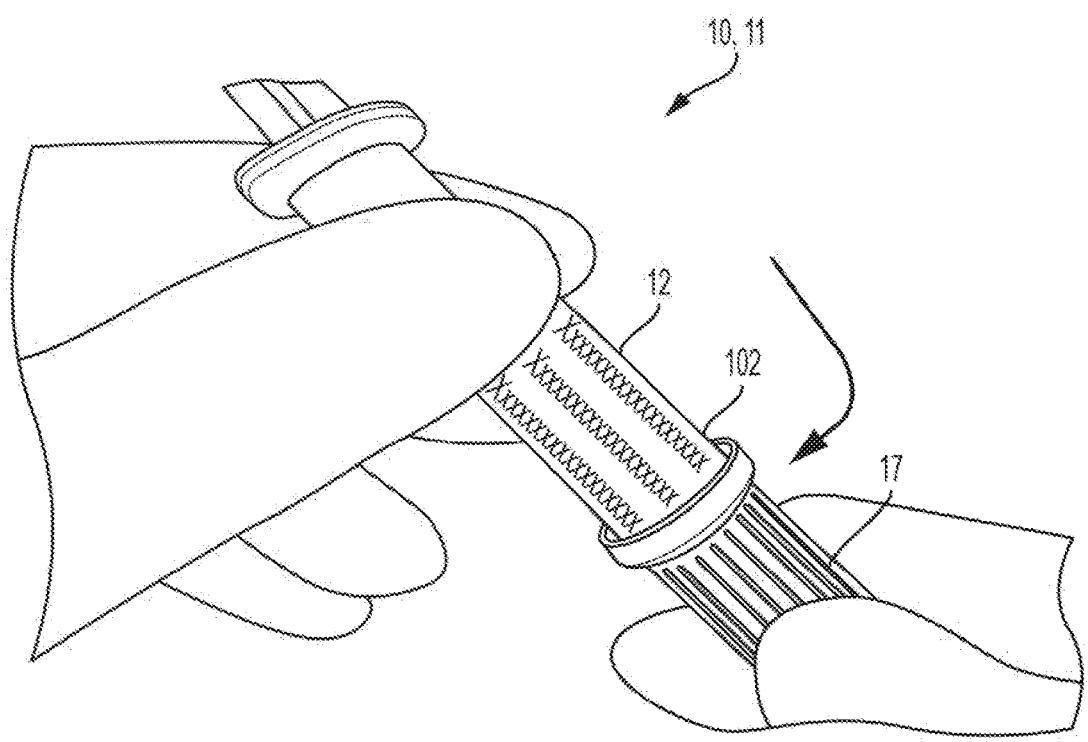
FIG. 37 is a perspective view of a sixth step of using a device of the present disclosure in accordance with an embodiment of the present invention.

Referring to FIG. 36, the cap 17 is removed from the tube 12 so that the syringe 13 is accessible. Next, referring to FIG. 37, the open end of the cap 17 can be placed on the closed distal end 102 of the tube 12.

Figure 38:
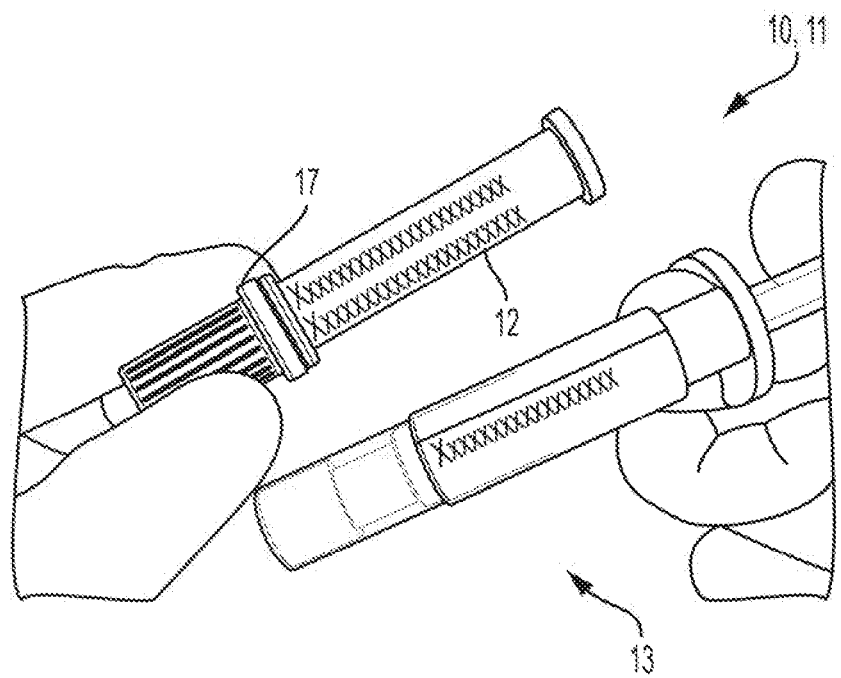
FIG. 38 is a perspective view of a seventh step of using a device of the present disclosure in accordance with an embodiment of the present invention.
Figure 39:
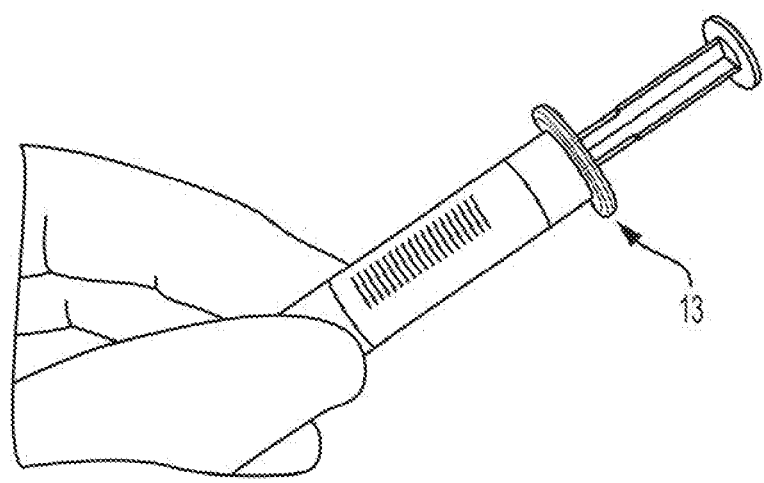
FIG. 39 is a perspective view of an eighth step of using a device of the present disclosure in accordance with an embodiment of the present invention.

Referring to FIG. 38, the syringe 13 can be removed from the packaging assembly 11. Next, the cap 17, the tube 12, and the tamper evident sleeve of the film 18 can be discarded. Before using the syringe 13, referring to FIG. 39, a visual inspection of the syringe 13 can be done by verifying important information.

Advantageously, after a proper inspection of the syringe 13 is performed, the syringe 13 is ready to be administered immediately upon removal of the packaging assembly 11.

Figure 40:
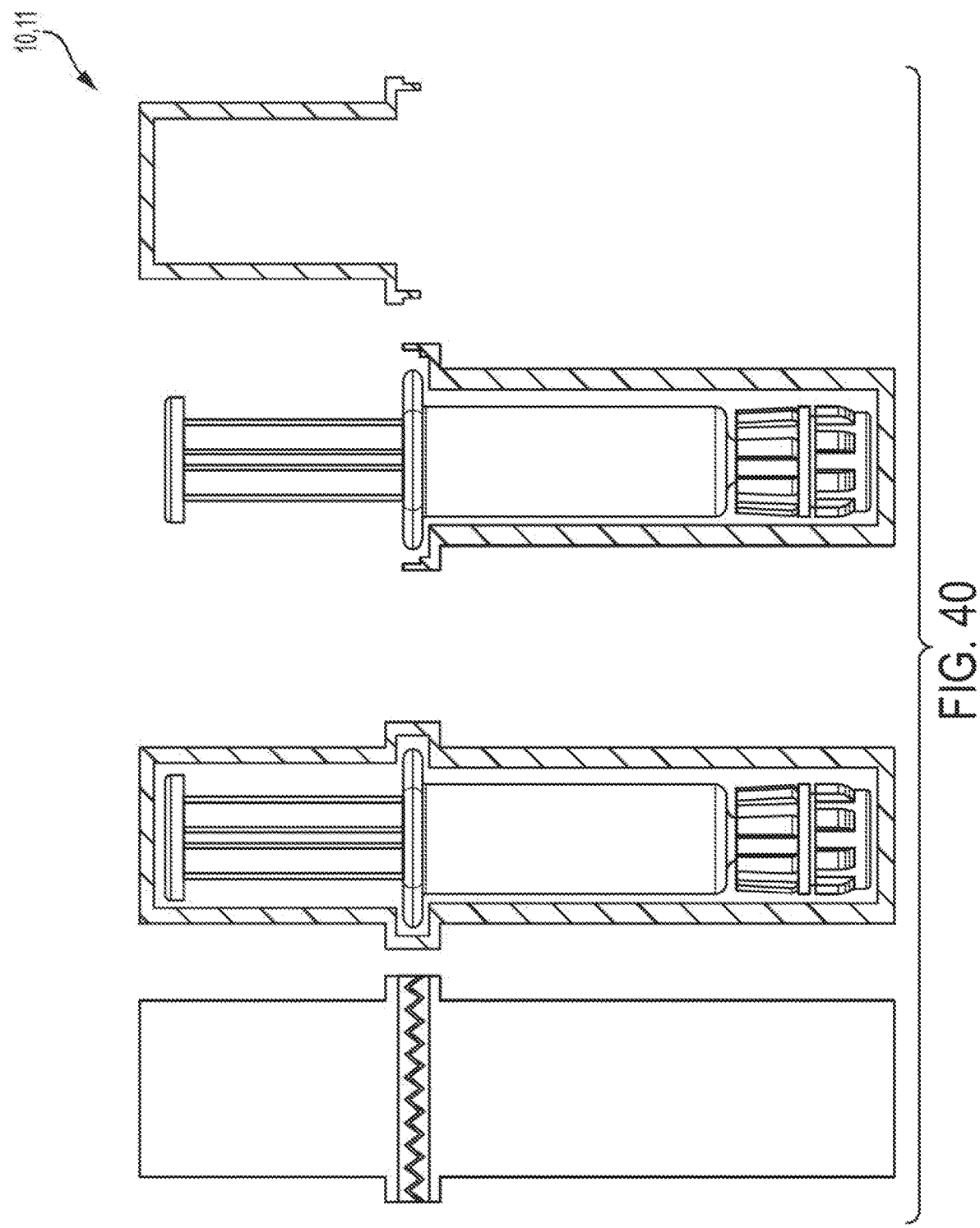
FIG. 40 are views of a syringe packaging system in accordance with another embodiment of the present invention.
Figure 41:
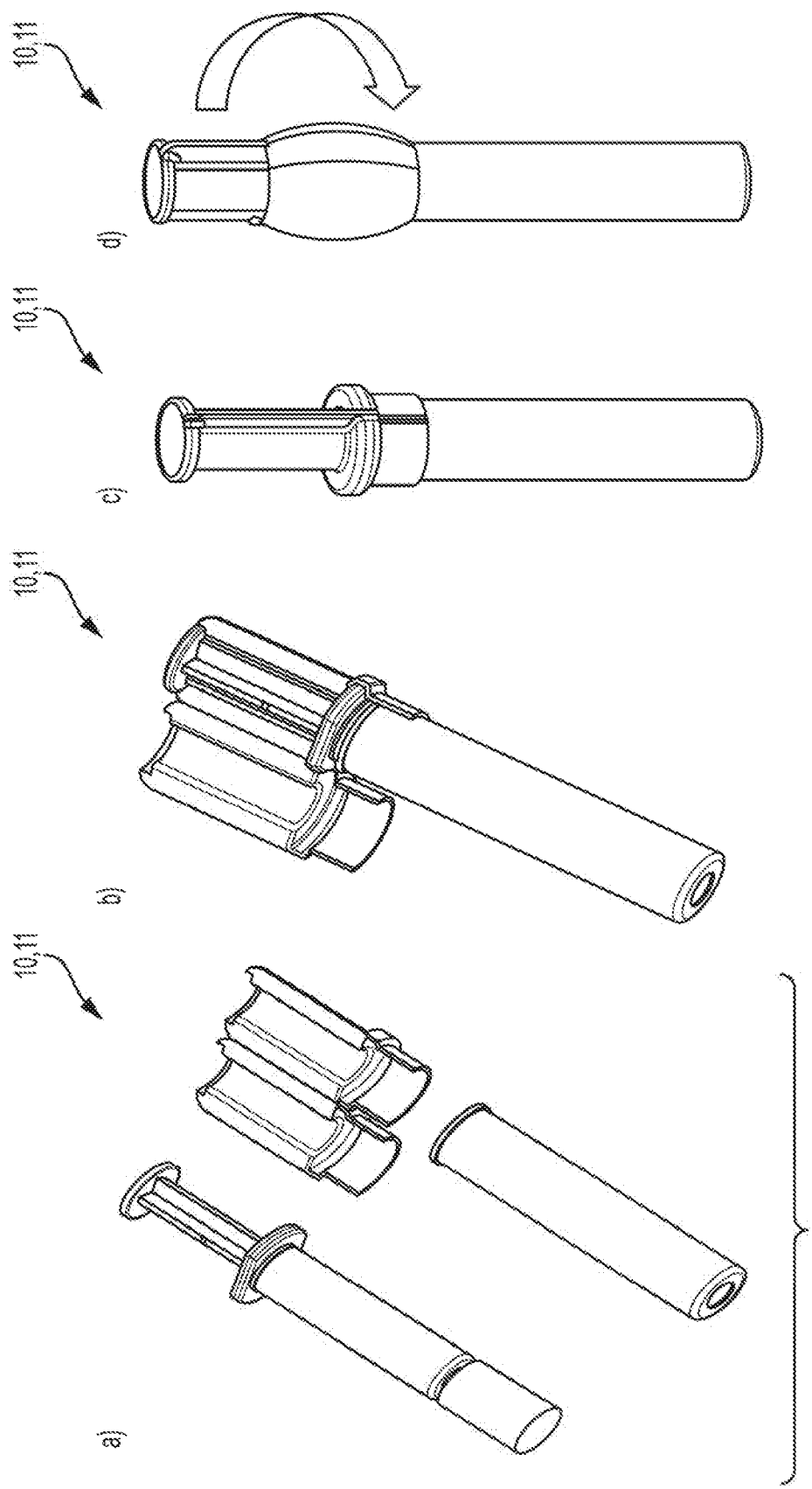
FIG. 41 are views of a syringe packaging system in accordance with another embodiment of the present invention.

FIGS. 40 and 41 illustrate other alternative exemplary embodiments of a packaging assembly 11 of the present disclosure.

Figure 42:
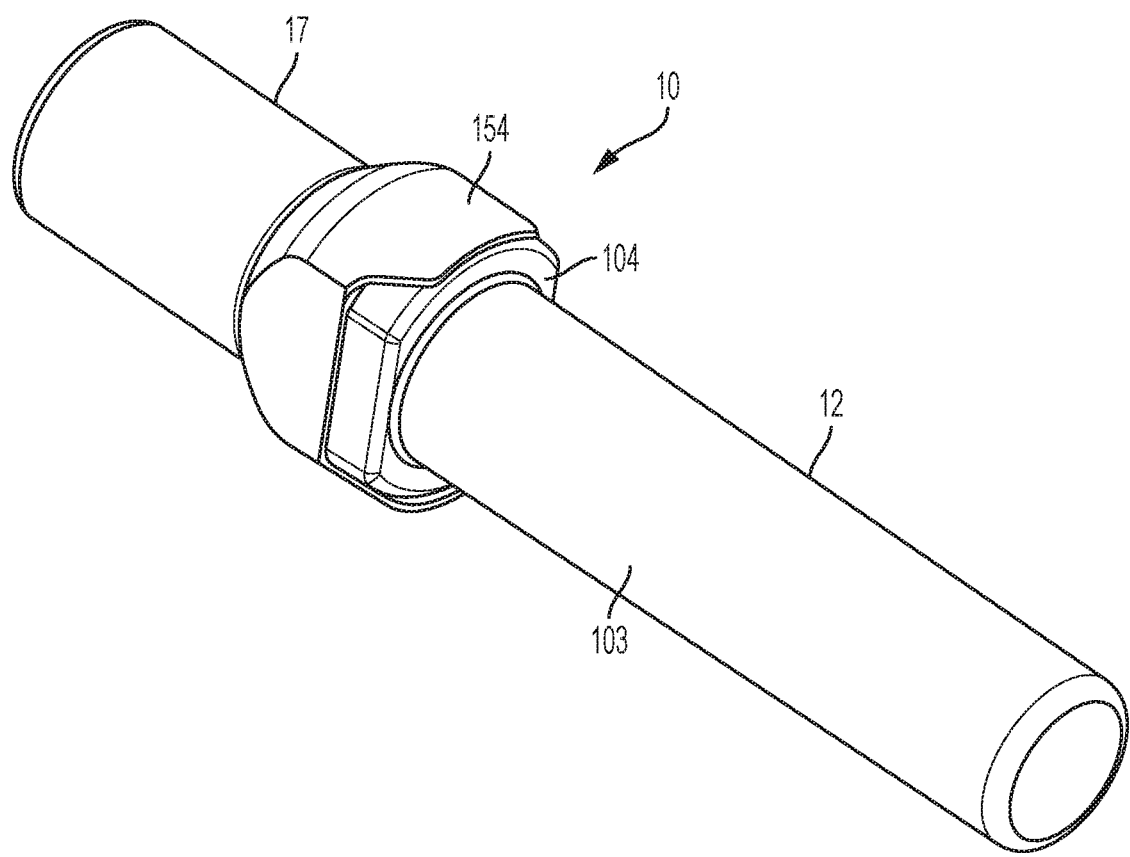
FIG. 42 is a perspective view of a syringe packaging system in accordance with another embodiment of the present invention.
Figure 43:
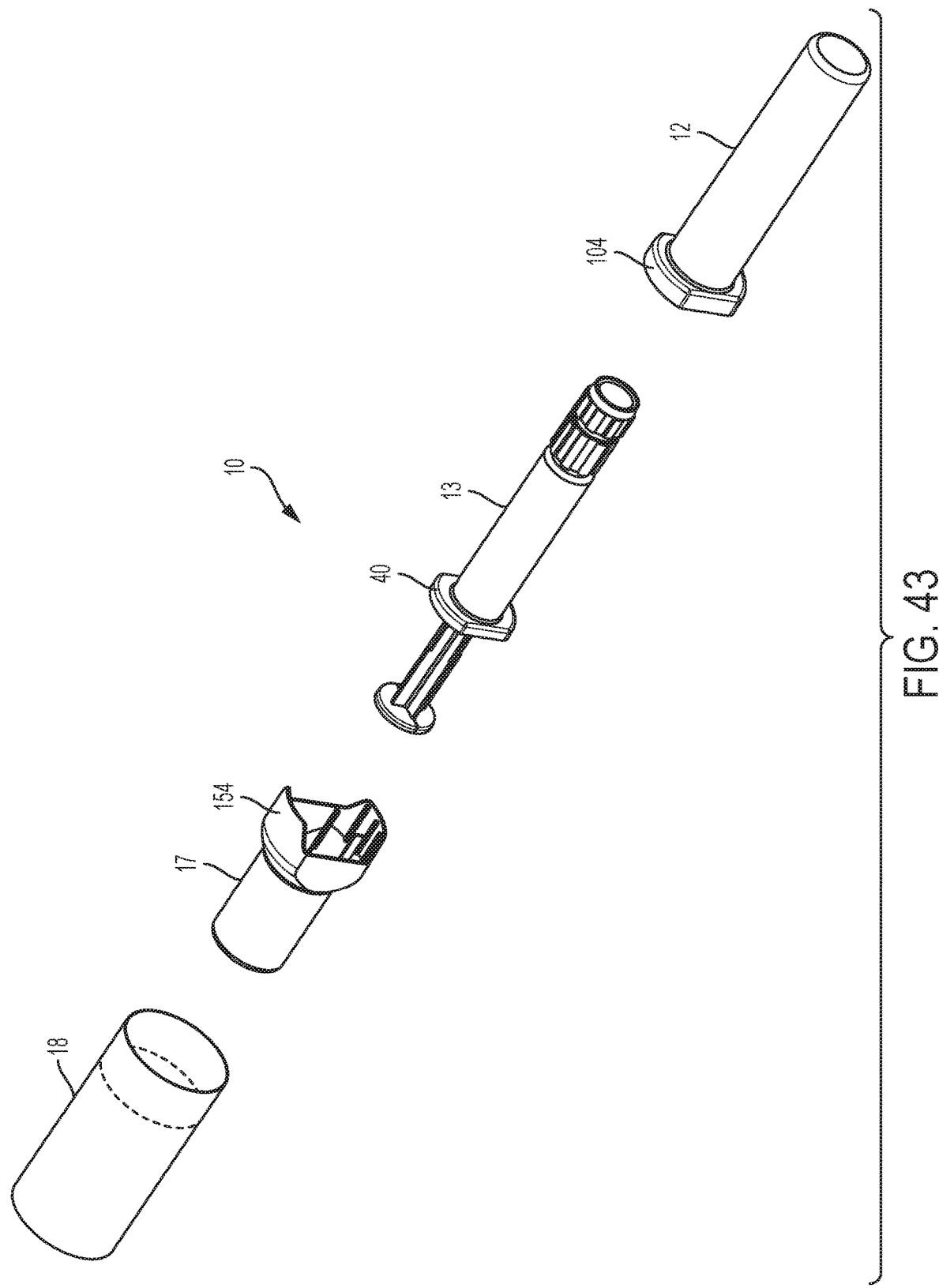
FIG. 43 is an exploded perspective of a syringe packaging system in accordance with an embodiment of the present invention.

A further embodiment of a syringe packaging system 10 in accordance with the invention is shown in FIGS. 42-50. For ease of reference, elements similar to elements of earlier described embodiments are given the same reference numbers in FIGS. 42-50. Similar to earlier described embodiments, the syringe packaging system 10 of FIGS. 42-50 generally includes a tube 12 and cap 17 as well as a shrinkable film 18 (shown only in FIG. 43) that connects the tube 12 and the cap 17. Additionally, as in earlier embodiments, the tube 12 and cap 17 may provide a storage space for a syringe assembly 13 as shown in FIG. 43.

Figure 44:
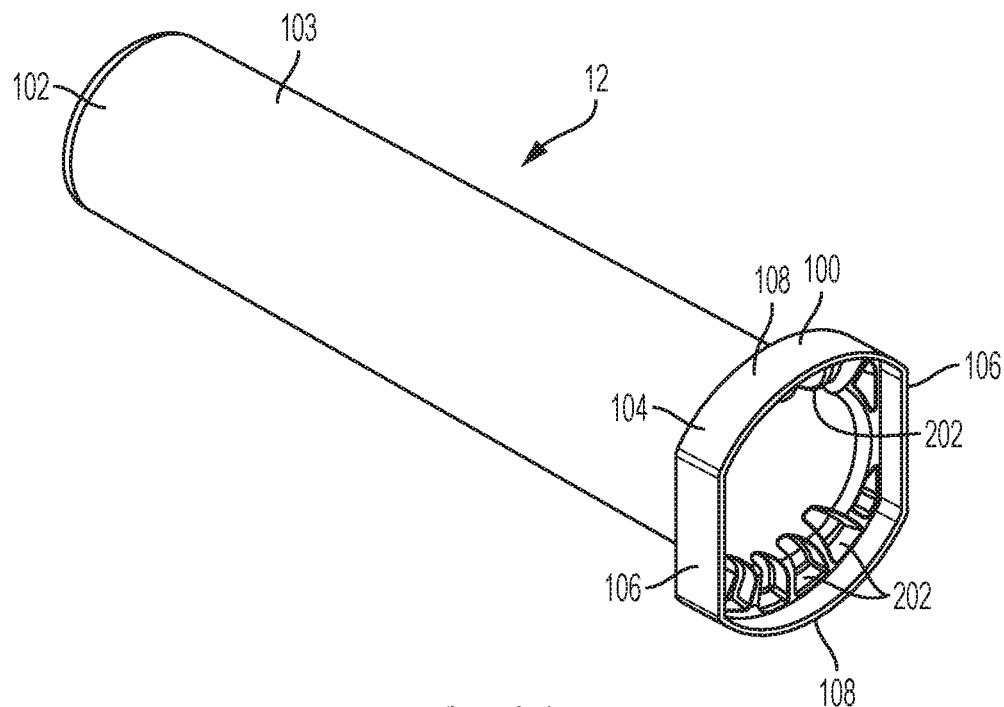
FIG. 44 is a perspective view of the tube of the embodiment of FIGS. 42-43.
Figure 46:
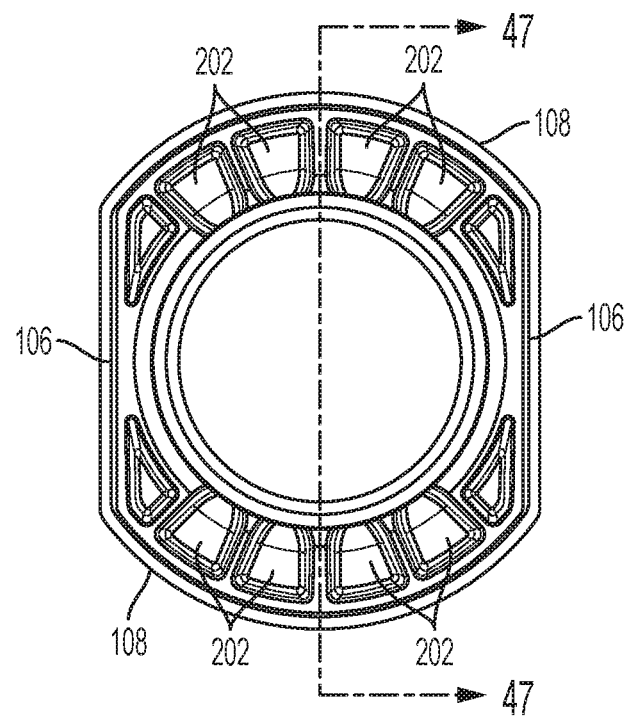
FIG. 46 is an end view of the tube of FIG. 44.
Figure 47:
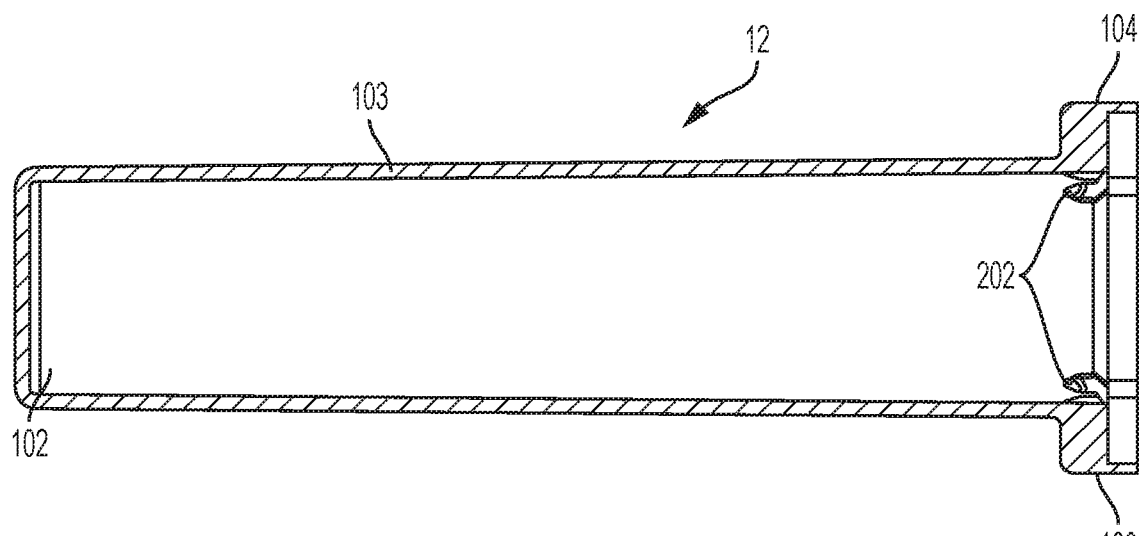
FIG. 47 is a cross-sectional view taken of the tube of FIG. 44 taken in the plane of line 47-47 in FIG. 46.

Referring to FIGS. 44, 46 and 47, the open proximal end 100 of the tube 12 may include a plurality of ribs 202. More specifically, the ribs 202 may be arranged on the interior surface of the tube 12 near the proximal end 100 of the tube 12 as best shown in FIGS. 44 and 47. These ribs 202 may provide several advantages. For example, the ribs 202 may provide the tube 12 with improved stability as well as provide a better seat for the syringe barrel flange 40. Moreover, the ribs 202 may help improve manufacturability of the tube 12, for example, by reducing deformation and easing ejection of the tube 12 from a molding tool.

Figure 45:
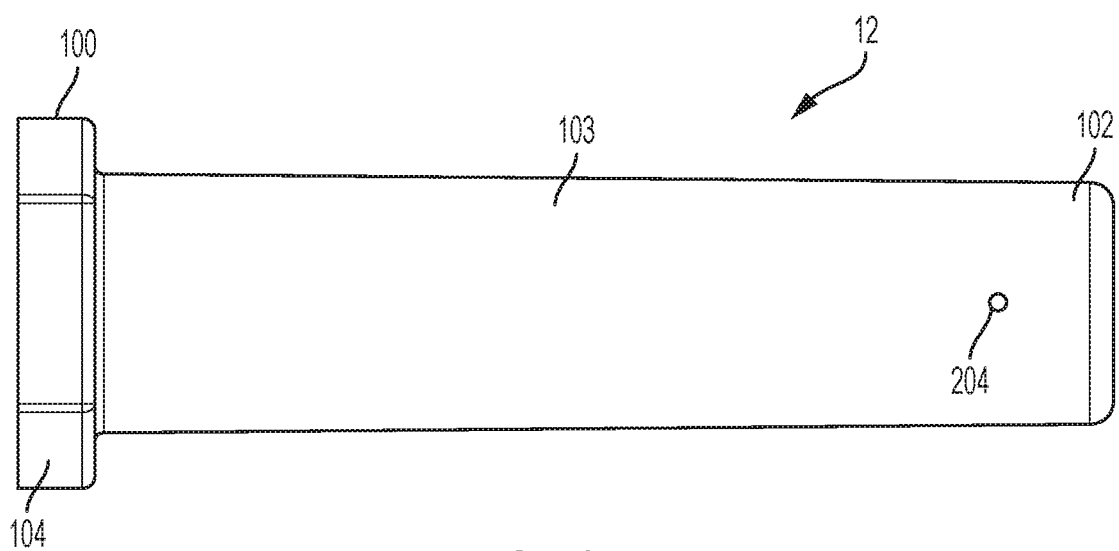
FIG. 45 is a side view of the tube of FIG. 44.

In the illustrated embodiment, the ribs 202 are arranged on the opposing arcuate wall portions 108 of the tube 12 while no ribs are provided on the opposing flat wall portions 106 of the tube 12 as best shown in FIG. 45. Eight ribs 202 in total are provided with four being provided in spaced relation from each other on each arcuate wall portion 106 of the tube 12, although more or less ribs 202 may be provided. In other embodiments, the ribs 202 are arranged on the arcuate wall portions 108 and the flat wall portions 106. In some embodiments, the ribs 202 are spaced in relation from each other on each arcuate wall portion 108 and each flat wall portion 106. In general, providing additional ribs 202 will provide the tube 12 with more stability. As shown in FIG. 46, the illustrated ribs 202 have a generally tapered configuration in which the width of the rib 202 decreases as it extends away from the interior surface of the tube 12. The number, arrangement and configuration of the ribs 202 may vary depending on the overall configuration and/or desired characteristics of the tube 12 and/or syringe barrel 14.

Improved stability and manufacturability of the tube 12 also may be provided in ways other than through the addition of ribs 202 to the interior of the proximal end 100 of the tube 12. For example, the tube 12 may be made of a material that provides increased stiffness and stability. Additionally, a plurality of gussets may be provided with each gusset extending between the exterior surface of the tube 12 and the underside of the tube flange 104. These gussets may be in addition to or in place of the plurality of ribs 202.

To improve manufacturability, the tube 12 may be configured to taper as it extends from the proximal end 100 to the distal end 102. More specifically, the sidewall 103 of the tube 12 may continuously taper as it extends from the proximal end 100 of the tube 12 to the distal end 102 of the tube as best shown in FIG. 45. According to one embodiment, the taper may be relatively small such as, for example, approximately 0.5°, 1°, 2°, 3°, 4°, 5°, or any range therein.

However, larger or smaller tapers may be provided as desired depending, for example, on the particular manufacturing equipment being used.

As shown in FIG. 45, the sidewall 103 of the tube 12 has an opening or gate 204 which represents the opening in the mold where the plastic is inserted. Positioning the gate 204 on the sidewall 103 of the tube 12 is advantageous because it helps prevent diversion and/or tampering with the syringe 13 contained within the tube 12. For example, if the gate 204 were arranged on the end wall at the distal end 102 of the tube 12, it may be possible to insert a needle through the gate 204 and withdraw the drug from the syringe by piercing the seal at the syringe tip cap. Providing the gate 204 on the sidewall 103 of the tube 12 prevents such a scenario because a needle that is inserted through the gate 204 on the sidewall 103 cannot reach the syringe tip cap. In the illustrated embodiment, the gate 204 is positioned on the sidewall 103 of the tube 12 closer to the proximal end 100 thereof; however, the gate 204 may be provided at other locations on the sidewall 103 of the tube 12 depending, for example, on the plastic injection molding equipment being used.

Figure 48:
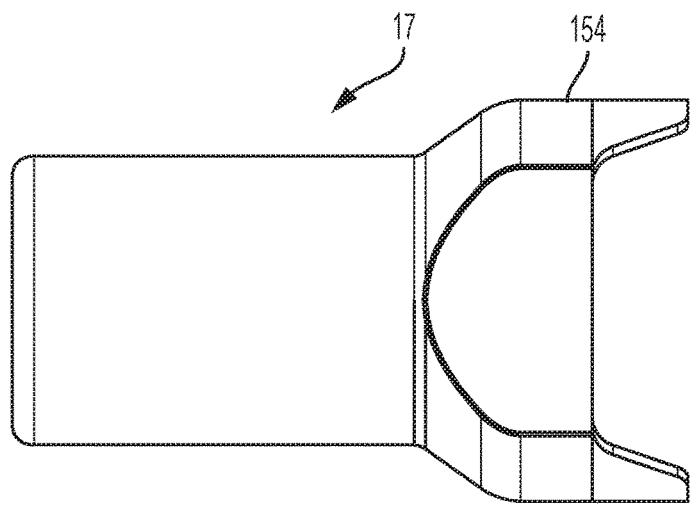
FIG. 48 is a side view of the cap of the embodiment of FIGS. 42-43.
Figure 49:
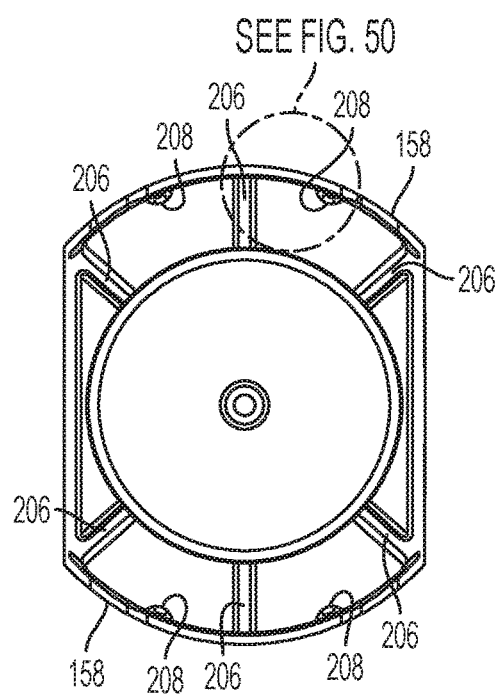
FIG. 49 is an end view of the cap of FIG. 48.
Figure 50:
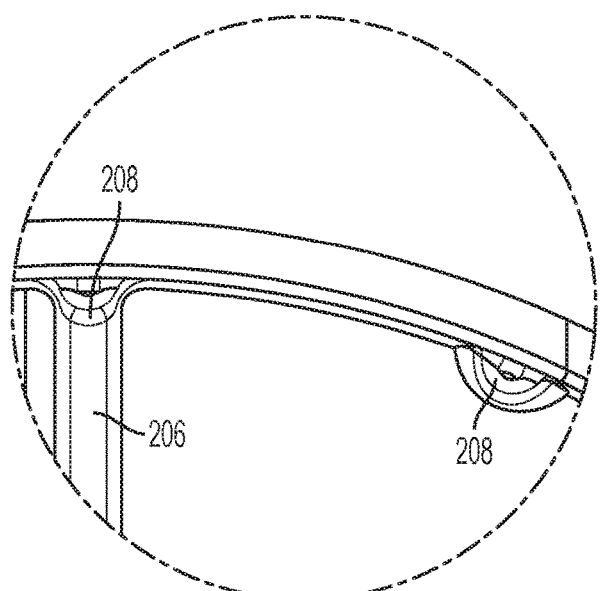
FIG. 50 is an enlarged end view of a portion of the cap of FIG. 48.

The cap 17 of the FIGS. 42 and 43 of the syringe packaging system 10 is shown in more detail in FIGS. 48-50. With reference to FIG. 48, the cap 17 is generally similar to the cap shown in the embodiment of FIG. 17 except that the edge of the cutout portion of the cut skirt 154 has more of a C-shaped configuration (featuring a rounded upper edge) when viewed from the side as compared to the U-shaped configuration of the cutout portion of the cut skirt 154 in the embodiment of FIG. 17 (featuring a straight upper edge). Moreover, the cap 17 of FIG. 48 is configured such that when it is assembled on the tube 12, the lower (or distal) edge of the cut skirt 154 is arranged below the lower edge of the tube flange 104 (see FIG. 42). The illustrated C-shaped configuration of the cutout portion and the extension of the cap skirt 154 below the tube flange 104 can help improve automated assembly of the cap 17 and tube 12. In other embodiments, the cap 17 is configured such that when it is assembled on the tube 12, the distal edge of the cut skirt 154 is flush with the lower edge of the tube flange 104. In yet other embodiments, the cap 17 is configured such that when it is assembled on the tube 12, the distal edge of the cut skirt 154 is arranged above the lower edge of the tube flange 104.

To provide stability to the cap 17 and reduce deformation during molding, the cap 17 may include a plurality of internal ribs 206. In the illustrated embodiment, the internal ribs 206 are arranged on the inside of the arcuate wall portions 158 of the cap 17 as shown in FIG. 49. In this case, there are a total of six internal ribs 206 with three spaced apart internal ribs 206 being provided on each arcuate wall portion 158. The number, arrangement and configuration of the internal ribs 206 may vary depending on the overall configuration and/or desired characteristics of the cap 17.

As shown in FIGS. 49 and 50, the cap 17 may further include a plurality of crush ribs 208 that are relatively smaller in dimension than the internal ribs 206. The crush ribs 208, which are best shown in FIG. 50, are configured to interfere with the outer surface of the tube 12, e.g., the tube cut flange 104, and assist in holding the cap 17 in place on the tube 12 after assembly. In the illustrated embodiment, there are six crush ribs 208 with three crush ribs being arranged in spaced relation on the interior of each of the arcuate wall portions 158. Other numbers, arrangements and configurations of crush ribs 208 may be provided depending on the configuration and/or desired characteristics of the cap 17 and/or tube 12.

In one embodiment, one or more protrusions may be provided on the exterior surface of the sidewall 103 of the tube 12 and/or cap 17. These protrusions may be arranged and configured to engage or grab the shrinkable film 18 and thereby prevent rotation of the film 18 relative to the tube 12 and/or cap 17 when a user is attempting to open the assembly. For example, the protrusions could be the gussets described above that extend between the exterior surface of sidewall 103 of the tube 12 and the underside of the tube flange 104.

Figure 51:
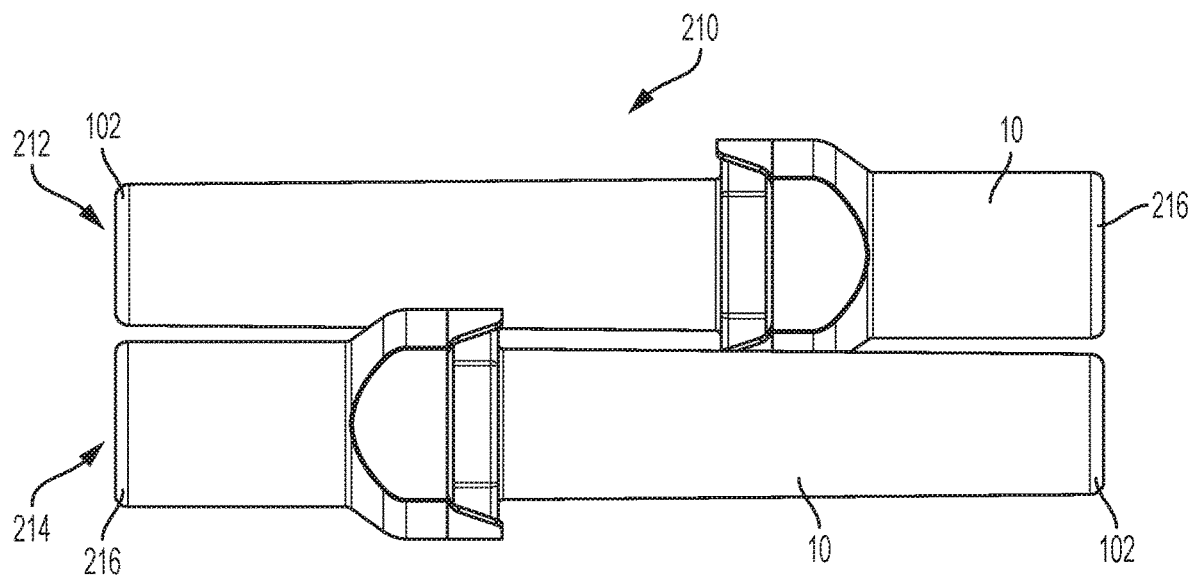
FIG. 51 is a side view of a syringe packaging system bundle in accordance with an embodiment of the present invention.
Figure 52:
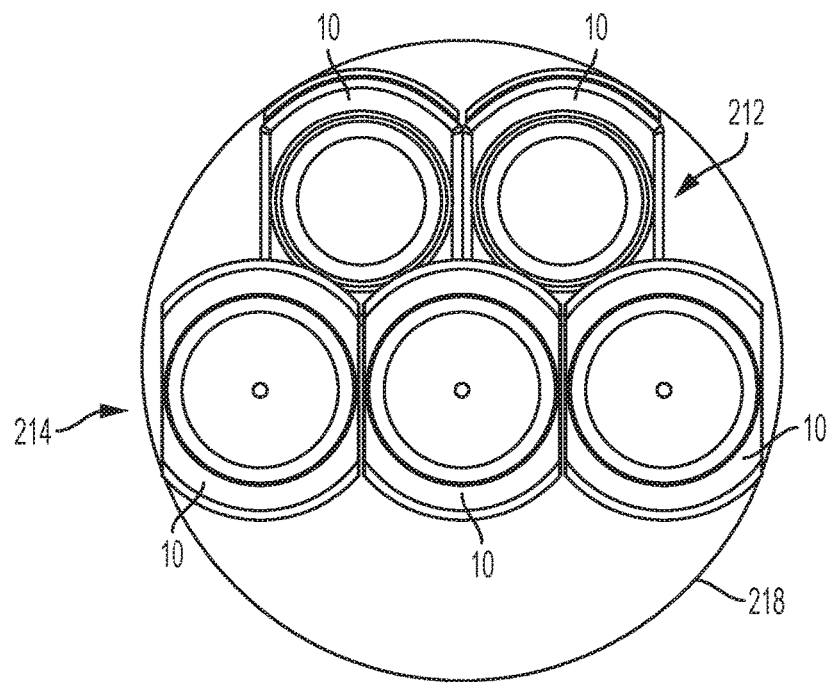
FIG. 52 is an end view of the syringe packaging system bundle of FIG. 51.

A further embodiment of a bundle 210 of syringe packaging systems 10 according to the present invention is shown in FIGS. 51 and 52. The bundle 210 arrangement shown in FIGS. 51 and 52 can permit the use of reduced storage space for the syringe packaging systems 10, which can be particularly advantageous in, for example, automated dispensing cabinets. The illustrated syringe packaging system bundle 210 includes a total of five syringe packaging systems 10 stacked in a two-row array. The first, in this case upper, row 212 of the bundle 210 includes two syringe packaging systems 10 while the second, in this case lower, row 214 of the bundle 210 includes three packaging systems 10. The syringe packaging systems 10 of the first row 212 are arranged parallel, but in the opposite orientation, to the syringe packaging systems 10 of the second row 214. In other words, the distal ends 102 of the tubes 12 of the packaging systems 10 of the first row 212 are aligned with the proximal end 216 of the caps 17 of the first row 214 while the proximal ends 216 of the caps 17 of the first row 214 are aligned with the distal ends 102 of the tubes 12 of the second row 214 as shown in FIG. 51. The two rows 212, 214 of the bundle 210 of syringe packaging systems 10 may be held together via a shrink wrap type material 218.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A syringe packaging system, comprising:
   a pre-filled syringe including a syringe barrel having a proximal end, a distal end, and a sidewall extending there between and defining a chamber, the proximal end having a syringe barrel cut flange; and
   a packaging member enclosing the pre-filled syringe, the packaging member including a tube having a proximal end and a closed distal end, the proximal end including a tube cut flange with first and second arcuate wall portions with each arcuate wall portion having a plurality of ribs, wherein the tube includes a sidewall extending between the proximal end and the distal end and the sidewall includes an injection molding gate.

2. The syringe packaging system of claim 1, wherein the plurality of ribs associated with each of the first and second arcuate wall portions are located in an interior of the tube.

3. The syringe packaging system of claim 1, wherein the tube cut flange includes a first flat wall portion and a second flat wall portion.

4. The syringe packaging system of claim 1, further comprising a cap having a first end and a second end, the second end including a cut skirt.

5. The syringe packaging system of claim 4, wherein the cut skirt of the cap includes a plurality of crush ribs configured to interfere with an outer surface of the tube when the cap is assembled on the tube.

6. The syringe packaging system of claim 4, wherein the cut skirt includes a flat wall portion and an arcuate wall portion.

7. The syringe packaging system of claim 4, wherein, with the pre-filled syringe enclosed within the packaging member, the cut skirt of the cap surrounds the syringe barrel cut flange.

8. The syringe packaging system of claim 7, wherein the packaging member further includes a film securable to a portion of the tube and a portion of the cap to connect the tube and the cap with the pre-filled syringe enclosed within the cap and the tube.

9. The syringe packaging system of claim 4, wherein the packaging member includes a film securable to a portion of the tube and a portion of the cap to connect the tube and the cap with the pre-filled syringe enclosed within the cap and the tube.

10. The syringe packaging system of claim 1, wherein the tube includes a sidewall extending between the proximal end and distal end of the tube and wherein the tube tapers as it extends from the proximal end to the distal end.

11. A syringe packaging system, comprising:
a pre-filled syringe including a syringe barrel having a proximal end, a distal end, and a sidewall extending therebetween and defining a chamber, the proximal end having a syringe barrel cut flange; and
a packaging member enclosing the pre-filled syringe, the packaging member comprising:
a tube having a proximal end and a distal end, the proximal end including a tube cut flange; and
a cap having a first end and a second end, the second end including a cut skirt with first and second arcuate wall portions each having a plurality of internal ribs, wherein the first and second arcuate wall portions of the cap each include a plurality of crush ribs that are relatively smaller than the internal ribs and are configured to interfere with an outer surface of the tube when the cap is assembled on the tube.

12. The syringe packaging system of claim 11, wherein the distal end of the tube is closed.

13. The syringe packaging system of claim 12, wherein the tube includes a sidewall extending between the proximal end and the distal end and the sidewall includes an injection molding gate.

14. The syringe packaging system of claim 11 wherein the packaging member further includes a film securable to a portion of the tube and a portion of the cap to connect the tube and the cap with the pre-filled syringe enclosed within the cap and the tube.

15. The syringe packaging system of claim 11, wherein the cut skirt includes first and second flat wall portions.

16. The syringe packaging system of claim 11, wherein, with the pre-filled syringe enclosed within the packaging member, the cut skirt of the cap surrounds the syringe barrel cut flange.

17. The syringe packaging system of claim 11, wherein the cut skirt has a cutout portion with an edge that has a C-shaped configuration.

18. A syringe packaging system, comprising:
a pre-filled syringe including a syringe barrel having a proximal end, a distal end, and a sidewall extending therebetween and defining a chamber, the proximal end having a syringe barrel cut flange; and
a packaging member enclosing the pre-filled syringe, the packaging member comprising:
a tube having a proximal end and a distal end, the proximal end including a tube cut flange having a plurality of ribs; and
a cap having a first end, a second end, the second end including a cut skirt having a plurality of internal ribs, and plurality of crush ribs that are relatively smaller than the internal ribs and which are configured to interfere with an outer surface of the tube when the cap is assembled on the tube, wherein when the pre-filled syringe is enclosed within the packaging member, the cut skirt of the cap surrounds the syringe barrel cut flange,
wherein the packaging member further includes a film that maintains together and connects the tube and the cap with the pre-filled syringe enclosed within the cap and the tube.

* * * * *